US006831069B2

(12) United States Patent
Tam et al.

(10) Patent No.: US 6,831,069 B2
(45) Date of Patent: Dec. 14, 2004

(54) PYRROLO[2,3-D]PYRIMIDINE NUCLEOSIDE ANALOGS

(75) Inventors: Robert Tam, Irvine, CA (US); Guangyi Wang, Irvine, CA (US); Johnson Lau, Newport Beach, CA (US); Zhi Hong, Mission Viejo, CA (US)

(73) Assignee: Ribapharm Inc., Costa Mesa, CA (US)

( * ) Notice: Subject to any disclaimer, the term of this patent is extended or adjusted under 35 U.S.C. 154(b) by 0 days.

(21) Appl. No.: 09/797,549

(22) Filed: Feb. 28, 2001

(65) Prior Publication Data

US 2002/0035077 A1 Mar. 21, 2002

Related U.S. Application Data

(63) Continuation-in-part of application No. PCT/US00/22674, filed on Aug. 17, 2000.
(60) Provisional application No. 60/182,676, filed on Feb. 15, 2000, and provisional application No. 60/151,233, filed on Aug. 27, 1999.

(51) Int. Cl.[7] ..................... A61K 31/34; A61K 31/381; C07D 487/04
(52) U.S. Cl. ........................ 514/43; 514/49; 536/27.2; 544/280
(58) Field of Search ...................... 544/280; 536/27.2; 514/43, 49

(56) References Cited

U.S. PATENT DOCUMENTS 5,506,347 A    4/1996  Erion et al.
5,665,721 A    9/1997  Bhagwat et al.
5,674,998 A    10/1997 Boyer et al.
6,455,508 B1 * 9/2002  Ramasamy et al. ........... 514/43

FOREIGN PATENT DOCUMENTS

| WO | WO98/39342 | 9/1998 |
|----|------------|--------|
| WO | WO98/39343 | 9/1998 |
| WO | WO98/39344 | 9/1998 |
| WO | WO99/45016 | 9/1999 |

OTHER PUBLICATIONS

Kim et al., Chem. Abstract 116:33911, 1991.*
Wang et al., Synthesis and Cytokine Modulation Properties of Pyrrolo[2,3-d]-4-pyrimidone Nucleosides, J. Med. Chem., vol. 43, No. 13, pp. 2566-2574, Jun. 2000.*
Bonnet et al., "Modulation of Leukocyte Genetic Expression by Novel Purine Nucleoside Analogues. A New Approach to Antitumor and Antiviral Agents", J. of Med. Chem. (Mar. 19, 1993), vol. 36, No. 6, pp. 625-653.
Hinshaw et al., "Pyrrolopyrimidine Nuclesodes. V. A Study on the Relative Chemical Reactivity of the 5-Cyano Group of the Nucleoside Antibiotic Toyocamycin and Desamino-toyocamycin. The Synthesis of Analogs of Sangivamycin", J. Org. Chem., No. 92, p. 236-421, (Apr 3, 1970).

* cited by examiner

*Primary Examiner*—Deepak Rao
(74) *Attorney, Agent, or Firm*—Brown Raysman Millstein Felder & Steiner, LLP

(57) ABSTRACT

Compositions and methods for pyrrolo[2,3-d]pyrimidine nucleoside analogs having substituents at the C4' and C5' positions of the ribofuranose moiety are presented. Contemplated compositions exhibit, among other things, anti-cancer and immunomodulating effects at reduced cytotoxicity.

7 Claims, 27 Drawing Sheets a R = Me   b R = ethynyl   c R = vinyl   d R = allyl

10 X = NH₂, Y = CN
11 X = OH, Y = CN
12 X = OH, Y = C(=NH)OMe
13 X = OH, Y = C(=NOH)NH₂
14 X = OH, Y = C(=NH)NH₂
15 X NH₂, Y = C(=NH)OMe a R = methyl   b R = vinyl
c R = ethyl    d R = HOCH$_2$ a R = Me   b R = ethynyl   c R = vinyl
d R = ethyl   e R = allyl   f R = propyl

| Table 1. Cytotoxicity of Analogues of the pyrrolo[2,3-d]pyrimidine nucleoside - MTS assay | | | | | | |
|---|---|---|---|---|---|---|
| | Prostate Cancer | Normal Fibroblasts | Melanoma Cancer | Lung Cancer | Ovarian R | Ovarian NR |
| Structure | EC50[uM] | EC50[uM] | EC50[uM] | EC50 | EC50 | EC50 |
| 61 | 12.5 | 50 | 40 | 34 | | |
| 59 | >100 | >100 | >100 | >100 | | |
| 44 | 0.07 | 0.08 | 0.06 | 0.02 | | |
| 57 | 0.01 | 0.08 | 0.01 | 0.06 | | |
| 48 | >100 | NT | >100 | >100 | | |
| 46 | 60.1 | NT | >100 | 99.3 | | |
| 53 | 98 | 39 | 82.5 | 97.5 | | |
| 10 | >100 | NT | >100 | >100 | | |
| 15 | >100 | NT | >100 | >100 | | |
| 26a(5'-R) | >100 | >100 | >100 | >100 | | |
| 27a(5'-R) | >100 | >100 | >100 | >100 | | |
| 23a(5'-S) | 44.2 | 45.6 | 51.8 | 30.1 | | |
| 21a(5'-S) | 98.2 | >100 | >100 | 90.9 | | |
| 23a(5'-R | 20.4 | 45.5 | 43.9 | 24.8 | 12.1 | 43.4 |
| 21a(5'-R) | >100 | >100 | | NT | | |
| 24a(5'-S) | >100 | 39.6 | 87.3 | 80.7 | | |
| 24a(5'-R0 | 70.1 | 34.9 | 70.1 | 30.8 | | |
| 49 | 5.6 | 3.3 | NT | NT | 5.7 | 5.1 |
| 64 | 4.3 | 2.3 | NT | NT | 4.4 | 3.7 |
| 50 | >100 | >100 | >100 | >100 | | |
| 51 | >100 | >100 | | | | |
| 23e(5'-R) | 50.6 | >100 | | | | |
| 23f(5'-R) | 45.9 | >100 | | | | |

Figure 9

Table 2

| Prostate Cancer Cells, HTB81 | | | | | | | | | | | | |
|---|---|---|---|---|---|---|---|---|---|---|---|---|
| Conc. (uM) | Untreated | 25a(5-S) | 26a(5-S) | 27a(5-S) | 25a(5-R) | 26a(5-R) | 27a(5-R) | 23a(5-S) | 21a(5-S) | 23a(5-R) | 21a(5-R) | |
| 100 | | 3.28 | 4.79 | 3.11 | 5.42 | 5.62 | 3.2 | 0.88 | 0.81 | 0.74 | 1.52 | |
| 50 | | 3.41 | 5.34 | 4.16 | 5.24 | 5.3 | 4.89 | 1.2 | 2.54 | 0.89 | 3.18 | |
| 25 | | 3.86 | 5.24 | 3.84 | 5.1 | 5.3 | 5.39 | 2.1 | 4.4 | 1.15 | 3.76 | |
| 12.5 | | 3.69 | NT | 3.96 | 5.35 | 5.2 | 5.37 | 2.9 | 4.3 | 3.23 | 3.9 | |
| 6.25 | | 3.62 | NT | 3.9 | 5.5 | NT | 5.6 | 3.16 | 4.5 | 3.5 | 4.2 | |
| 1.56 | | 3.6 | NT | 4.2 | 5.8 | NT | NT | 4.9 | 4.9 | 3.8 | 4.97 | |
| 0.78 | | 3.61 | NT | 4.56 | 6.1 | NT | 5.9 | 5.3 | 5.3 | 4.82 | 5.3 | |
| 0 | 5.78 | | | | | | | | | | | |

| Normal Cells/Human Fibroblasts | | | | | | | | | | | | |
|---|---|---|---|---|---|---|---|---|---|---|---|---|
| 100 | | 3.6 | 4.35 | 1.47 | 4.19 | 4.31 | 2.33 | 0.93 | 3.65 | 1.29 | 3.75 | |
| 50 | | 3.7 | 4.56 | 4 | 4.29 | 4.35 | 4.1 | 1.33 | 4.3 | 1.89 | 4.1 | |
| 25 | | 4.32 | 4.63 | 4.32 | 4.14 | 4.6 | 4.3 | 4.5 | 4.5 | 4.7 | 4.2 | |
| 12.5 | | 4.26 | 4.55 | 4.2 | 4.32 | 4.9 | 5.1 | 5.1 | 4.6 | 4.6 | 4.4 | |
| 6.25 | | 4.16 | 4.35 | 4.1 | NT | 5 | 5 | 5 | 4.5 | 4.8 | 4.6 | |
| 1.56 | | 4.36 | 4.43 | NT | NT | 5.2 | 5.2 | 5 | 4.4 | 4.7 | 4.5 | |
| 0.78 | | 4.26 | 4.38 | NT | NT | 5.3 | 5.1 | 5 | 4.6 | 4.7 | 4.7 | |
| 0 | 4.47 | | | | | | | | | | | |

Figure 10

Nucleoside concentration (μM)

ICN 17739 Induces a Type 2 Cytokine Bias in T cells from RA Patients and Normal Donors

Lane
1 Resting
2 Activated
3 + 10μM 17739
4 + 10μM 17465

PYRROLO[2,3-D]PYRIMIDINE NUCLEOSIDE ANALOGS

This application is a continuation in part (CIP) of PCT/US00/22674, filed Aug. 17, 2000, which claims the benefit of 60/151,233, filed Aug. 27, 1999; and of new PCT application entitled "Nucleoside Analogs With Carboxamidine Modified Bicyclic Base," filed on Feb. 15, 2001 by Guangyi Wang, Robert Tam, Zhi Hong, and Johnson Lau, which claims the benefit of 60/182,676, filed Feb. 15, 2000; all of which are incorporated herein by reference in their entirety.

FIELD OF THE INVENTION

The field of the invention is nucleoside analogs.

BACKGROUND OF THE INVENTION

Nucleoside analogs have long been used as antimetabolites for treatment of cancers and viral infections. After entry into the cell, nucleoside analogs are frequently phosphorylated by nucleoside salvage pathways, in which the analogs are typically phosphorylated to the corresponding mono-, di-, and triphosphates. Among other intracellular destinations, triphosphorylated nucleoside analogs often are used as substrate for DNA or RNA polymerases and consequently incorporated into DNA or RNA. Where triphosphorylated nucleoside analogs are strong polymerase inhibitors, they may induce premature termination of a nascent nucleic acid molecule. Where triphosphorylated nucleoside analogs are incorporated into nucleic acid replicates or transcripts, gene expression or disruption of function may result.

On a more cellular level, the nucleoside analogs can also interfere with the cell cycle, and especially desirable effects of nucleoside analogs include induction of apoptosis of cancer cells. Furthermore, nucleoside analogs are also known to modulate certain immune responses.

Various nucleoside analogs with relatively potent anticancer activity are known in the art. For example, known drugs include thymidylate synthase inhibitors such as 5-fluorouridine, adenosine deaminase inhibitors, including 2-chloroadenosine, and neplanocin A, which is an inhibitor of S-adenosylhomocysteine hydrolase. However, all or almost all of the known nucleoside analogs also imply a threat to normal mammalian cells, primarily because these nucleoside analog's lack adequate selectivity between normal cells and tumor cells. Unfortunately, lack of adequate selectivity is frequently associated with severe side effects, and therefore often limits the potential of such analog therapeutics.

Although there are various nucleoside analogs known in the art, all or almost all of them, suffer from one or more disadvantages. Therefore, there is still a need to provide improved methods and compositions for nucleoside analogs.

SUMMARY OF THE INVENTION

The present invention is directed to nucleoside analogs with modifications on the sugar moieties of the pyrrolo[2,3-d]pyrimidine nucleoside analogs, which can significantly reduce the toxicity of the nucleoside analogs to the mammalian cells while they also provide significant cytotoxicity to cancer cells. These modifications include but are not limited to substitutions at the C4' and C5' positions of ribofuranose moieties. The present invention also demonstrates that certain pyrrolo[2,3-d]pyrimidine nucleoside analogs have desired immunomodulation effects, including enhancement of Type 1 cytokines such as IL-2 and suppression of Type 2 cytokines such as IL-4. These immunomodulation properties can be useful in anticancer, antiviral and autoimmune diseases, treating inflammation and preventing graft rejection.

In one aspect of the inventive subject matter, the nucleoside analog is a pyrrolo[2,3]-pyrimidine nucleoside having a structure according to the formula (I):

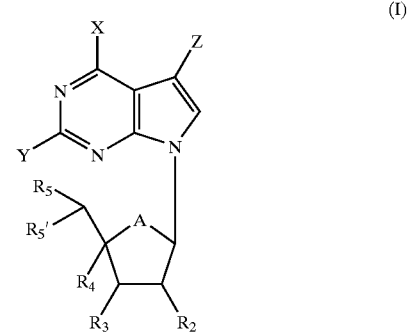

(I)

wherein A is O, S, or CH2; X is H, $NH_2$ or OH; Y is H, halogen or $NH_2$; Z is selected from the group consisting of H, halogen, R, OH, OR, SH, SR, $NH_2$, NHR, $NR_2$, CN, $C(O)NH_2$, COOH, COOR, $CH_2NH_2$, $C(=NOH)NH_2$, and $C(=NH)NH_2$, where R is alkyl, alkenyl, alkynyl, or aralkyl; $R_2$ and $R_3$ are independently selected from the group consisting of H, F, and OH; $R_4$ is selected from the group consisting of a hydrogen, an alkyl, an alkenyl, an alkynyl, and an aralkyl, wherein $R_4$ optionally has at least one of a heteroatom and a functional group; $R_5$ is H, OH, OP(O)$(OH)_2$, P(O)$(OH)_2$, OP(O)$(OR')_2$, or P(O)$(OR')_2$, wherein R' is a masking group; and $R_{5'}$ is selected from the group consisting of an alkyl, an alkenyl, an alkynyl, and an aralkyl, wherein $R_{5'}$ has at least two carbon atoms, and optionally has at least one of a heteroatom and a functional group.

In another aspect of the inventive subject matter, the nucleoside analog is a pyrrolo[2,3d]pyrimidine nucleoside having a structure according to the formula (II):

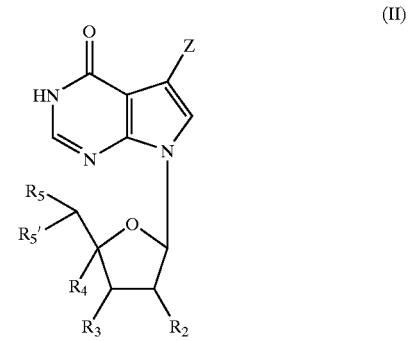

(II)

wherein Z is CN, $C(O)NH_2$, $C(=NH)NH_2$, or $C(=NOH)NH_2$ and $R_4$ and $R_{5'}$ are independently selected from the group consisting of a hydrogen, an alkyl, an alkenyl, an alkynyl, and an aralkyl, wherein $R_4$ and $R_{5'}$, independently and optionally contain at least one of a heteroatom and a functional group; with the proviso that $R_4$ and $R_{5'}$ are not together hydrogen.

In a further aspect of the inventive subject matter, the nucleoside analog is a pyrrolo[2,3]pyrimidine nucleoside having a structure according to the formula (III), which may advantageously be in a salt form (e.g., an HCl salt):

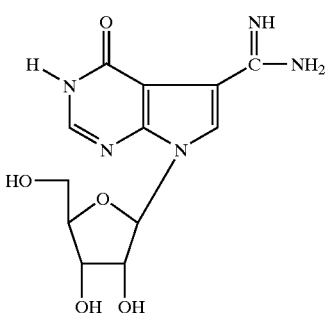

(III)

In still further aspects of the inventive subject matter, contemplated compounds are utilized to inhibit tumor growth or to modulate Type 1 and Type 2 cytokine, chemokine production, and in treatment of autoimmune diseases. It is further contemplated that compounds according to the inventive subject matter may be used in the treatment of any condition which responds positively to administration of the compound, and a pharmaceutical composition may comprise contemplated compounds (where appropriate in a prodrug form) or a pharmaceutically acceptable ester or salt thereof admixed with at least one pharmaceutically acceptable carrier.

Various objects, features, aspects and advantages of the present invention will become more apparent from the following detailed description of preferred embodiments of the invention, along with the accompanying drawings.

BRIEF DESCRIPTION OF THE DRAWING

FIG. 9 is a table indicating cytotoxicity of various compounds according to the inventive subject matter.

FIG. 10 is a table indicating rates of DNA synthesis in cells treated with of various compounds according to the inventive subject matter.

DETAILED DESCRIPTION

Contemplated Compounds

Figure 1:
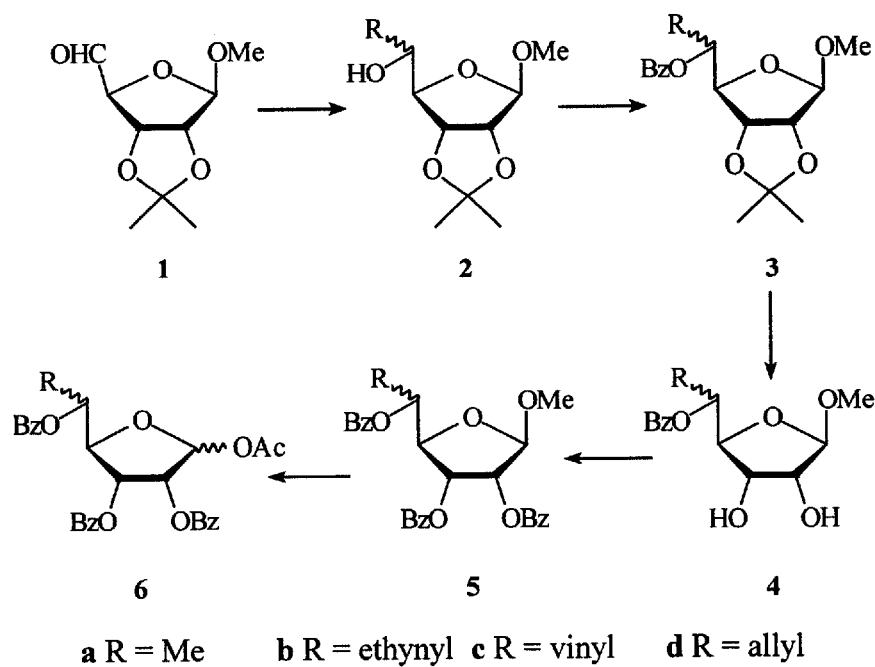
FIG. 1 is a first exemplary synthetic scheme of reactions included in the production of compounds according to the inventive subject matter.

Pyrrolo[2,3-d]pyrimidine nucleoside analogs according to the general formulae (I), (II), and (III) were found to have various biological effects on normal and hyperproliferative cells.

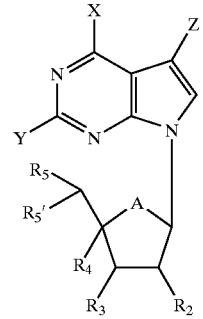

(I)

wherein A is O, S, or CH$_2$; X is H, NH$_2$ or OH; Y is H, halogen or NH$_2$; Z is selected from the group consisting of H, halogen, R, OH, OR, SH, SR, NH$_2$, NHR, NR$_2$, CN, C(O)NH$_2$, COOH, COOR, CH$_2$NH$_2$, C(=NOH)NH$_2$, and C(=NH)NH$_2$, where R is alkyl, alkenyl, alkynyl, or aralkyl; R$_2$ and R$_3$ are independently selected from the group consisting of H, F, and OH; R$_4$ is selected from the group consisting of a hydrogen, an alkyl, an alkenyl, an alkynyl, and an aralkyl, wherein R$_4$ optionally has at least one of a heteroatom and a functional group; R$_5$ is H, OH, OP(O)(OH)$_2$, P(O)(OH)$_2$, OP(O)(OR')$_2$, or P(O)(OR')$_2$, wherein R' is a masking group; and R$_{5'}$ is selected from the group consisting of an alkyl, an alkenyl, an alkynyl, and an aralkyl, wherein R$_{5'}$ has at least two carbon atoms, and optionally has at least one of a heteroatom and a functional group.

It should be especially appreciated that the terms "alkyl", "alkenyl", "alkynyl", and "aralkyl" as used herein refer to both linear and branched species. With respect to the substituents R$_2$ and R$_3$, it should be appreciated that both R$_2$ and R$_3$ may be independently directed to the α- or β-face. Furthermore, where the substituents on C$_{5'}$ are non-identical, substitution on C$_5$ may result in an R- or S-chiral center. The term "heteroatom", as used herein, refers to non-carbon atoms in an organic molecule, and particularly contemplated heteroatoms include halogens, nitrogen, oxygen, and sulfur. The term "functional group" as used herein refers to a reactive bond (e.g., double or triple bond) or reactive group (e.g., —OH, —SH, —NH$_2$, —N$_3$, —CN, COOH, —CHO, —CONH$_2$, etc.).

Particularly contemplated pyrrolo[2,3-d]pyrimidine nucleoside analogs are those according to formula (1) wherein Z is CN, C(O)NH$_2$, or C(=NH)NH$_2$, and wherein R$_{5'}$ has at least two carbon atoms and is selected from the group consisting of an alkyl, an alkenyl, an alkynyl, and an aralkyl.

The pyrrolo[2,3-d]pyrimidine nucleoside analog according to formula (II) has the following structure:

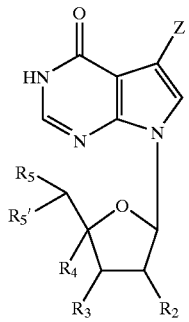

(II)

wherein Z is CN, C(O)NH$_2$, C(=NH)NH$_2$, or C(=NOH)NH$_2$ and R$_4$ and R$_{5'}$ are independently selected from the group consisting of a hydrogen, an alkyl, an alkenyl, an alkynyl, and an aralkyl, wherein R$_4$ and R$_{5'}$ independently and optionally contain at least one of a heteroatom and a functional group; with the proviso that R$_4$ and R$_{5'}$ are not together hydrogen; and wherein the remaining substituents are as defined in formula (I).

The pyrrolo[2,3-d]pyrimidine nucleoside analog according to formula (III) has the following structure:

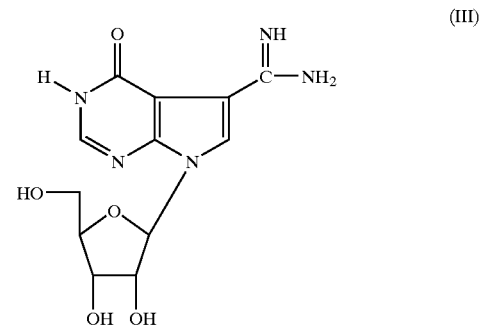

(III)

Alternatively, contemplated structures of compounds according to formula III (formula III analogs) may be modified to include heteroatoms and/or substituents as shown below.

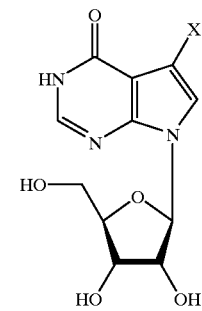

X = C(O)NH$_2$, C(=NOH)NH$_2$
C(=NH)NH$_2$, C(=NNH$_2$)NH$_2$
CH$_2$NH$_2$, C(S)NH$_2$

-continued

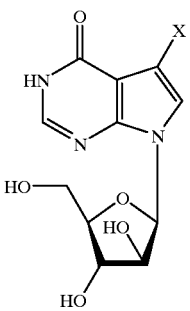

X = CN, C(=NOH)NH₂
C(=NH)NH₂, C(=NNH₂)NH₂
CH₂NH₂

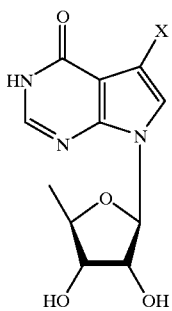

X = CN
C(=NOH)NH₂
C(=NH)NH₂

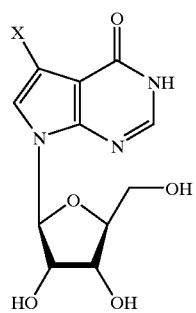

X = CN
C(=NOH)NH₂
C(=NH)NH₂

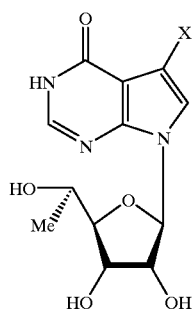

X = CN
C(=NOH)NH₂
C(=NH)NH₂

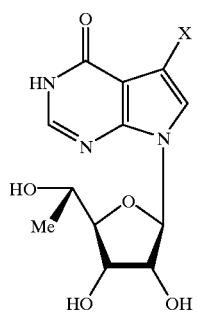

X = CN
C(=NOH)NH₂
C(=NH)NH₂

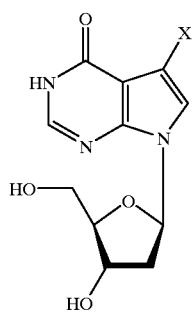

X = CN
C(=NH)NH₂

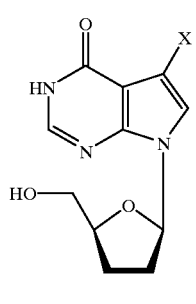

X = CN
C(=NOH)NH₂
C(=NH)NH₂

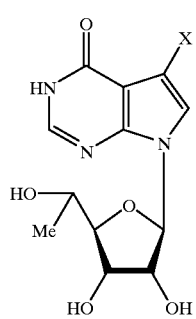

X = CN
C(=NH)NH₂

Still further contemplated alternative compounds include compounds according to formula IV:

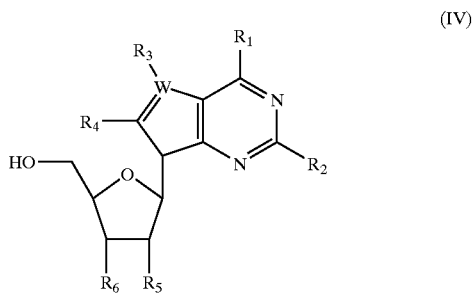

(IV)

wherein $R_1$ is a halogen, OH, NHR, C(NH)(NHR), or $N_3$; $R_2$ is NHR, C(NH)(NHR), C≡CR, or R; W is N or C; $R_3$ is halogen, CN, $CONH_2$, C≡CR, H, $N_3$, CHO, COOH, or COOR; $R_4$ is halogen, $N_3$, CN, NHR, C≡CR, or R; $R_5$ and $R_6$ are independently H, OH, $CH_3$, $NH_2$, or OR; wherein R is a substituted or unsubstituted alkyl, aryl, alkenyl, alkaryl, which may or may not be branched. The sugar moiety in compounds according to formula IV may also include a sulfur atom or may be a $C_4$-sugar, a cyclobutyl, or a cyclopropyl.

It should still further be appreciated that all contemplated nucleoside analogs may be in D-configuration or in L-configuration, and it is particularly contemplated that, where appropriate, contemplated compounds may be in a prodrug form or in a salt form (e.g., HCl salt, HBr salt, or hydrogen phosphate salt).

It should be appreciated, however, that compounds according to the inventive subject matter may also be in forms and formulations other than previously described, and especially contemplated forms include prodrug forms or otherwise modified forms in which contemplated molecules are chemically and/or enzymatically modified to improve pharmacological and/or pharmacodynamical properties, including higher specificity towards target organs, cells or subcellular compartments and increased half-life time in the organism.

For example, cholesterol adducts may be formed to increase target specificity towards the liver, or apolipoprotein adducts may be formed to enhance penetration of the modified drug across the blood brain barrier to the brain. In another example, receptor ligand complexes may be synthesized to target the modified drug to a particular cell expressing a receptor specific for the ligand. Alternatively, antibody or antibody fragment complexes may be formed to increase selective delivery of the modified drug to a subcellular location. There are many prodrug and modified forms known in the art, and particularly contemplated prodrug forms include prodrugs described in U.S. Provisional Application 60/216,418, filed Apr. 17, 2000, and incorporated herein by reference.

In still further examples, charged or uncharged groups, lipophilic or polar groups may be added to contemplated molecules to increase the half-life time in serum or other target organs and/or cells. In further examples, it should be appreciated that the contemplated compounds, where phosphorylated at the $C_5$ atom, may also be di-, or tri-phosphorylated, or incorporate a thiophosphate.

Particularly contemplated prodrug forms will advantageously achieve at least one of increased specificity towards a target organ or target cell, metabolic stability in compartments other than the target cell or organ, reduced toxicity, prolonged serum half-life time, increased uptake into specific cells and/or compartments, and enhanced physicochemical properties (increased solubility, neutralization or introduction of electrical charge, increased/decreased polarity and/or hydrophobicity), etc. There are various prodrug forms of nucleoside drugs known in the art, and contemplated prodrug forms may include modifications on the sugar moiety and/or the base. Depending on the particular compound and target, especially contemplated modifications may include formation of a tri-O-acetyl derivative of contemplated compounds, esterification of the 5'OH group on the sugar moiety to form a 5'-retinoyl derivative or derivative with alternative acids (synthesis as described in C. Sergheraert, C. Pierlot, A. Tartar, Y. Henin, M. Lemaitre, *J. Med. Chem.*, 36, 826–830, 1993). Alternatively, coumarin or aminoacid esters may be prepared from contemplated compounds. For specific delivery of drugs to the liver and the biliary system the endogenous bile acid transport system is an attractive candidate. Consequently, cholic acid esters may be prepared from contemplated compounds.

Where contemplated compounds are modified to form a nucleotide (i.e., include a 5'-phosphate group; e.g., as a monophophate, diphophate, or triphophate), protected 5'-phosphate derivatives (e.g., cyclic and non-cyclic mono-, di-, and triesters) may be prepared, and particularly include amino acid phosphoramidates, salicylate phosphonic esters, and phosphonic esters with lipophilic compounds (modofoed and unmodified alkyl, alkenyl, cholersterol, etc). Other possible prodrugs include the possible combinations of the groups shown in PCT patent application WO 98/39342, WO 98/39343, WO 98/39344 and WO 99/45016. Prodrugs of contemplated compounds may also be obtained by derivatizing the amidine functionality, and especially preferred derivatives include substituted amides that are coupled to the carboxamide group of contemplated compounds. Further contemplated prodrug forms of nucleosides and their analogs are described in U.S. patent application No. 09/594,410 filed Jun. 16, 2000, which is incorporated by reference herein.

Further stereochemical aspects especially include R and S configurations at the $C_5$ atom where appropriate, and it should be appreciated that the substituents in contemplated compounds may be directed to α or β phase.

The term "protecting group" refers to a chemical group that is added to, oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The terms "immunomodulator" and "modulator" are herein used interchangeably and refers to natural or synthetic products capable of modifying the normal or aberrant immune system or immunocompetent cell (e.g., a T-cell, or antigen presenting cell) through stimulation or suppression.

Contemplated compounds may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the contemplated compounds. The term "α" and "β" indicate the specific stereochemical configuration of a substituent at an asymmetric carbon atom in a chemical structure as drawn. The term "enantiomers" refers to a pair of stereoisomers that are non-superimposable mirror images of each other. A mixture of a pair of enantiomers, in a 1:1 ratio, is a "racemic" mixture. The term "isomers" refers to different compounds that have the same formula. "Stereoisomers" are isomers that differ only in the way the atoms are arranged in space.

Administration of contemplated compounds

It is contemplated that compounds according to the present invention will be administered in any appropriate pharmaceutical formulation, and under any appropriate protocol. Thus, administration may take place orally, parenterally (including subcutaneous injections, intravenous, intramuscularly, by intrasternal injection or infusion techniques), by inhalation spray, rectally, or topically and so forth, and in dosage unit formulations containing conventional non-toxic pharmaceutically acceptable carriers, adjuvants and vehicles.

Thus, it should be appreciated that contemplated compounds can be formulated in various formulations, including liquid, syrup or gel forms (e.g., for injection, ingestion, or topical administration) and solid forms (e.g., for ingestion, injection, or deposition in a body cavity). For example, where it is contemplated that compounds according to the inventive subject matter are instable in the gastric environment, injection of a preferably isotonic solution is particularly contemplated. Alternatively, intranasal application or inhalation of a liquid form may be appropriate to circumvent acid degradation. On the other hand, where contemplated compounds are known to be resistant to digestive degradation, contemplated forms may be administered in form of a syrup or tablet. Depending on the particular use, contemplated compounds may also be formulated for topical or transdermal applications. There are many more formulations known in the art, all of which are also contemplated suitable in conjunction with the inventive subject matter presented herein, and particularly contemplated formulations are described in "Drug Products for Clinical Trials: An Intl. Guide to Formulation, Production, Quality Control" by Donald C. Monkhouse and Christopher T. Rhodes (Editors); ISBN:082479852X.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and amino acid ester derivatives, pyridine esters and various salt forms (especially the HCl salt) of the present compounds are preferred and can be administered in a method of treatment of a condition of a patient.

In addition, compounds according to the present invention may be administered alone or in combination with other agents for the treatment of infections or conditions (infra).

Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect. Preferably, the combination therapy involves the administration of one compound of the present invention or a physiologically functional derivative thereof and one of the agents mentioned herein below.

Examples of other drugs or active ingredients contemplated to be effective in combination with a contemplated compounds are anti-viral agents such as interferon, including but not limited to interferon α and γ, Ribavirin, acyclovir, and AZT™; anti-fungal agents such as tolnaftate, Fungizone™, Lotrimin™, Mycelex™, Nystatin and Amphoteracin; anti-parasitics such as Mintezol™, Niclocide™, Vermox™, and Flagyl™, bowel agents such as Immodium™, Lomotil™ and Phazyme™; anti-tumor agents such as interferon α and γ, Adriamycin™, Cytoxan™, Imuran™, Methotrexate, Mithracin™, Tiazofurin™, Taxol™; dermatologic agents such as Aclovate™, Cyclocort™, Denorex™, Florone™, Oxsoralen™, coal tar and salicylic acid; migraine preparations such as ergotamine compounds; steroids and immunosuppresants not listed above, including cyclosporins, Diprosone™, hydrocortisone, mycophenolic acid, Arava™ (Leflunomide); Floron™, Lidex™, Topicort and Valisone; and metabolic agents such as insulin, and other drugs which may not nicely fit into the above categories, including cytokines such as IL2, IL4, IL6, IL8, IL10 and IL12. Especially preferred primary drugs are AZT, 3TC, 8-substituted guanosine analogs, 2,3-dideoxynucleosides, interleukin II, interferons such as IαB-interferons, tucaresol, levamisole, isoprinosine and cyclolignans.

Examples of such further therapeutic agents include agents that are effective for the modulation of immune system or associated conditions such as AZT, 3TC, 8-substituted guanosine analogs, 2',3'-dideoxynucleosides, interleukin II, interferons, such as α-interferon, tucaresol, levamisole, isoprinosine and cyclolignans. Certain compounds according to the present invention may be effective for enhancing the biological activity of certain agents according to the present invention by reducing the metabolism or inactivation of other compounds and as such, are co-administered for this intended effect.

With respect to dosage, one of ordinary skill in the art will recognize that a therapeutically effective amount will vary with the infection or condition to be treated, its severity, the treatment regimen to be employed, the pharmacokinetics of the agent used, as well as the patient (animal or human) treated. It is generally contemplated that dosages will typically be in a range of between about 0.5 mg/kg to about 50 mg/kg, however, various alternative dosages are also appropriate, including dosages between 0.5 mg/kg and 0.1 mg/kg and less, but also dosages between 50 and 100 mg/kg (e.g., 125 mg/kg) and more. It is further contemplated that while treatment success may be achieved with some disease conditions at relatively low plasma concentrations of contemplated compounds, other disease conditions may require relatively high dosages.

With respect to the concentration of contemplated compounds, it is preferred that the concentration is in a range of approximately 1 $\mu$M to about 100 $\mu$M when measured at the site of action. However, and particularly where the affinity of contemplated compounds is below 1 $\mu$M, appropriate concentrations may also be in the range of 999 nM to 10 nM, and less. On the other hand, where contemplated compounds exhibit relatively short half-life times, or have a high turnover, contemplated concentrations may be 0.1 mM and 100 mM, and more. Thus, the dosage of contemplated compounds may vary significantly, but appropriate dosages can readily be determined in in vitro or animal experiments. Consequently, it should be appreciated that contemplated compounds will be in the serum/plasma at concentrations of about 10 nMol to 1 mM, and more typically in the range of 0.1 microM to 100 microM. Where contemplated compounds are accumulated in a target cell or target organ, the concentration of such compounds may be similar to plasma/serum concentrations, or significantly higher (e.g., at least two-fold, more preferably at least 5-fold, and most preferably at least 10-fold). It is contemplated, however, that an appropriate regimen will be developed by administering a small amount, and then increasing the amount until the side effects become unduly adverse or the intended effect is achieved.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

It should still further be appreciated that contemplated compounds and formulations may include functional and non-functional additives. For example, where transcutaneous drug delivery is desired, skin penetration enhancers may be added. Examples for non-functional additives include fillers, antioxidants, flavor, or color agents to enhance a particular quality of contemplated compounds.

Contemplated Uses

It is contemplated that compounds according to Formulae I–III will be used to treat a wide variety of conditions, and in fact any condition which responds positively to administration of contemplated compounds. Among other things it is specifically contemplated that compounds of the invention may be used to treat an infection, an infestation, a cancer or tumor or an autoimmune disease. It is further contemplated that the compounds of the invention may be used to target conditions or diseases in specific organs of a patient, such as the liver or heart.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles, and fungus.

Infestations contemplated to be treated with the compounds of the present invention include protozoan infestations, as well as helminth and other parasitic infestations.

Cancers or tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis, rheumatoid arthritis, rejection of transplantation, giant cell arteritis, allergy and asthma.

Still other contemplated uses of the compounds according to the present invention include use as intermediates in the chemical synthesis of other nucleoside or nucleotide analogs that are, in turn, useful as therapeutic agents or for other purposes.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Type 1 and Type 2 with respect to one another. Where modulation of Type 1 and Type 2 lymphokines occurs, it is particularly contemplated that the modulation may include suppression of both Type 1 and Type 2, or suppression of Type 1 and stimulation of Type 2.

For example, many autoimmune diseases (e.g., rheumatoid arthritis, multiple sclerosis, diabetes, inflammatory bowel disease, psoriasis, lupus erythematodes) and diseases characterized (at least in part) by activation of CD4$^+$ cells have been shown to correlate with a polarized type 1 cytokine expression. Contemplated compounds have been shown to be effective to induce type 2 cytokine expression, to reduce type 1 cytokine expression, and to reduce proliferation of activated T-cells (infra). Consequently, it should be appreciated that, among other things, contemplated compounds may advantageously be employed to treat diseases that are correlated with an increased type 1 cytokine expression, or diseases that are correlated with an decreased type 2 cytokine expression, or diseases that are correlated with an increased type 1 and decreased type 2 cytokine expression. Thus, particularly contemplated treatments using contemplated compounds include type 1 cytokine-mediated inflammatory responses and autoimmune diseases. Consequently, it should be appreciated that contemplated compounds may be employed as immunomodulators, and particularly as type 1 cytokine suppressants and/or as type 2 cytokine stimulant.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may attain because L-nucleosides may not be recognized by enzymes, and therefore may have longer half-lives.

Among the various biological effects of contemplated compounds, particularly significant biological effects include modulation of the Type 1 and Type 2 cytokine production, control of neoplastic conditions (i.e., reduction of DNA synthesis or reduction in cell growth), and reduction of chemokine and growth factor release as described below. Consequently, a contemplated method of changing secretion of a cytokine from a cell may comprise a step in which a compound according to formula (I-IV) is provided and has a further step in which the cell is presented with the compound according to formula (I-IV) at a concentration effective to change the secretion of the cytokine. While all possible combinations of substituents in formula (I-IV) are generally contemplated, particularly contemplated compounds are compounds according to formula (I) wherein $R_4$ and $R_{5'}$ are independently selected from the group consisting of a hydrogen, an alkyl, an alkenyl, an alkynyl, and an aralkyl, and wherein $R_4$ and $R_{5'}$ independently and optionally contain at least one of a heteroatom and a functional group, with the remaining substituents as defined above in formula (I). In an alternative aspect, the compound employed to change the secretion of a cytokine from a cell may also be a compound according to the following structure:

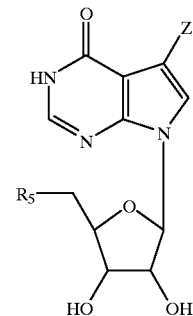

wherein Z is CN, C(O)NH$_2$, C(=NH)NH$_2$, C(=NNH$_2$)NH$_2$, or —C(=NOH)NH$_2$, and wherein $R_5$ is H, OH, OP(O)(OH)$_2$, P(O)(OH)$_2$, OP(O)(OR')$_2$, or P(O)(OR')$_2$, with R' being a masking group. Contemplated cytokines particularly include Type 1 (e.g., IL-2, TFN-α, IFNγ) and Type 2 (e.g., IL-4, IL-5, IL-13) cytokines. With respect to the cells, it is contemplated that all cells known to produce and/or secrete cytokines are appropriate, however, especially contemplated cells include lymphocytes and cancer cells (e.g., prostate cancer cells, infra).

In a further aspect of the inventive subject matter, a method of reducing growth of a hyperproliferative cell may comprise a step in which a compound according to formula (I) is provided, and another step in which the hyperproliferative cell is presented with the compound at a concentration effective to reduce the growth of the hyperproliferative cell. Particularly preferred compounds include compounds according to formula (I) wherein $R_4$ is selected from the group consisting of a hydrogen, an alkyl, an alkenyl, an alkynyl, and an aralkyl, wherein $R_4$ optionally contains at least one of a heteroatom and a functional group, and wherein $R_{5'}$ is selected from the group consisting of a hydrogen, an alkyl, an alkenyl, an alkynyl, and an aralkyl, wherein $R_{5'}$ has at least two carbon atoms, and optionally contains at least one of a heteroatom and a functional group, with the proviso that $R_4$ and $R_{5'}$ are not together hydrogen, and with the remaining substituents as defined above in formula (I). Particularly contemplated hyperproliferative cells include cancer cells, and an especially contemplated cancer cell is a prostate cancer cell. While not whishing to be bound to a particular theory, it is contemplated that the reduction of growth comprises reduction of nucleic acid synthesis (e.g., RNA and/or DNA).

In a still further aspect of the inventive subject matter, it is contemplated that a method of reducing a release of a growth factor from a cell has a step in which a compound according to formula (I) is provided, and another step in which the cell is presented with the compound at a concentration effective to reduce the release of the growth factor. It is contemplated that the release of various growth factors may be reduced by the method presented herein, however reduction of VEGF release is especially contemplated. Similarly, while all cells known to secrete growth factors are contemplated in conjunction with the method presented herein, particularly contemplated cells include cancer cells, and especially prostate cancer cells.

Synthesis of contemplated compounds

With respect to the synthesis of contemplated compounds, it should be appreciated that pyrrolo[2,3-d]pyrimidine nucleoside analogs according to the inventive subject matter can be synthesized via various synthetic routes, and the following procedures are provided by way of example only.

Synthesis of C5'-modified pyrrolo[2,3-d]pyrimidine nucleoside analogs

The 5'-substituted nucleoside analogs are prepared from the condensation of the pyrrolo[2,3-d]pyrimidine bases and the properly protected, 5'-substituted ribofuranoses. As shown in FIG. 1, Compound 1, prepared according to a published procedure (Jones et al. Methods in carbohydrate Chemistry (edited by Whistler and Moffat), vol. VI, pp315–322, Academic Press, New York, (1972)), was treated with a variety of nucleophiles such as Grignard reagents to give compound 2, which was benzoylated and subsequently treated with trifluoroacetic acid to give compound 4. Benzoylation and the following treatment with acetic anhydride/acetic acid in the presence of sulfuric acid to give compound 6, which was used for condensation with pyrrolo[2,3-d]pyrimidine bases.

Figure 2:
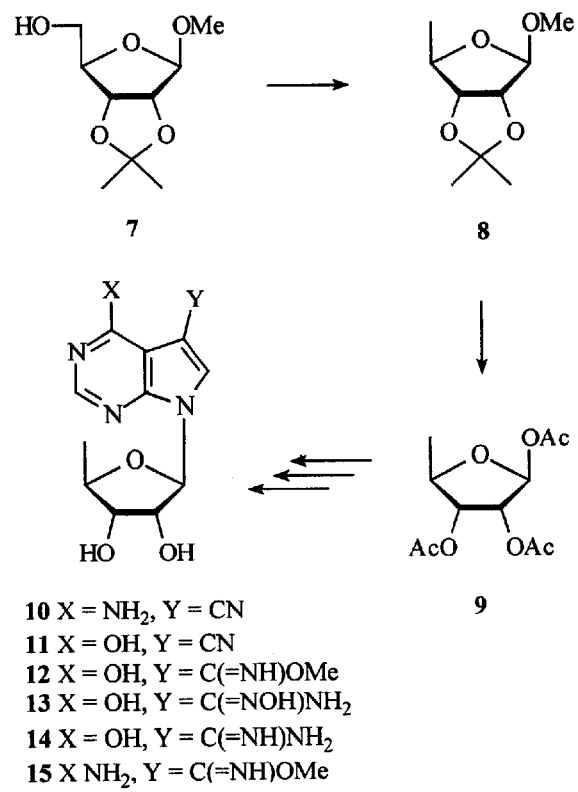
FIG. 2 is a second exemplary synthetic scheme of reactions included in the production of compounds according to the inventive subject matter.

Compound 7 (Jones et al. Methods in carbohydrate Chemistry (edited by Whistler and Moffat), vol. VI, pp315–322, Academic Press, New York, (1972)), prepared according to a published procedure, was converted to a tosylate derivative, which was reduced with lithium aluminum hydride to give compound 8. By similar procedures shown in FIG. 1, compound 8 was converted to compound 9. The condensation of 9 and the pyrrolo[2,3-d]pyrimidine 19 and the subsequent transformations as shown in scheme 2 gave compounds 10–15 as illustrated in FIG. 2.

Figure 3:
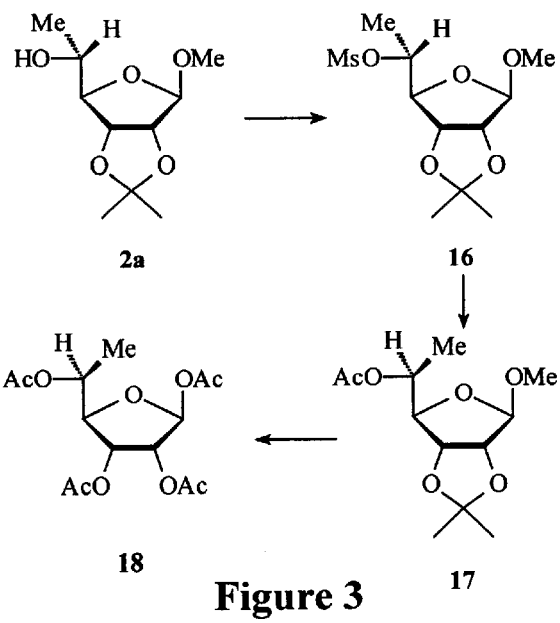
FIG. 3 is a third exemplary synthetic scheme of reactions included in the production of compounds according to the inventive subject matter.
Figure 4:
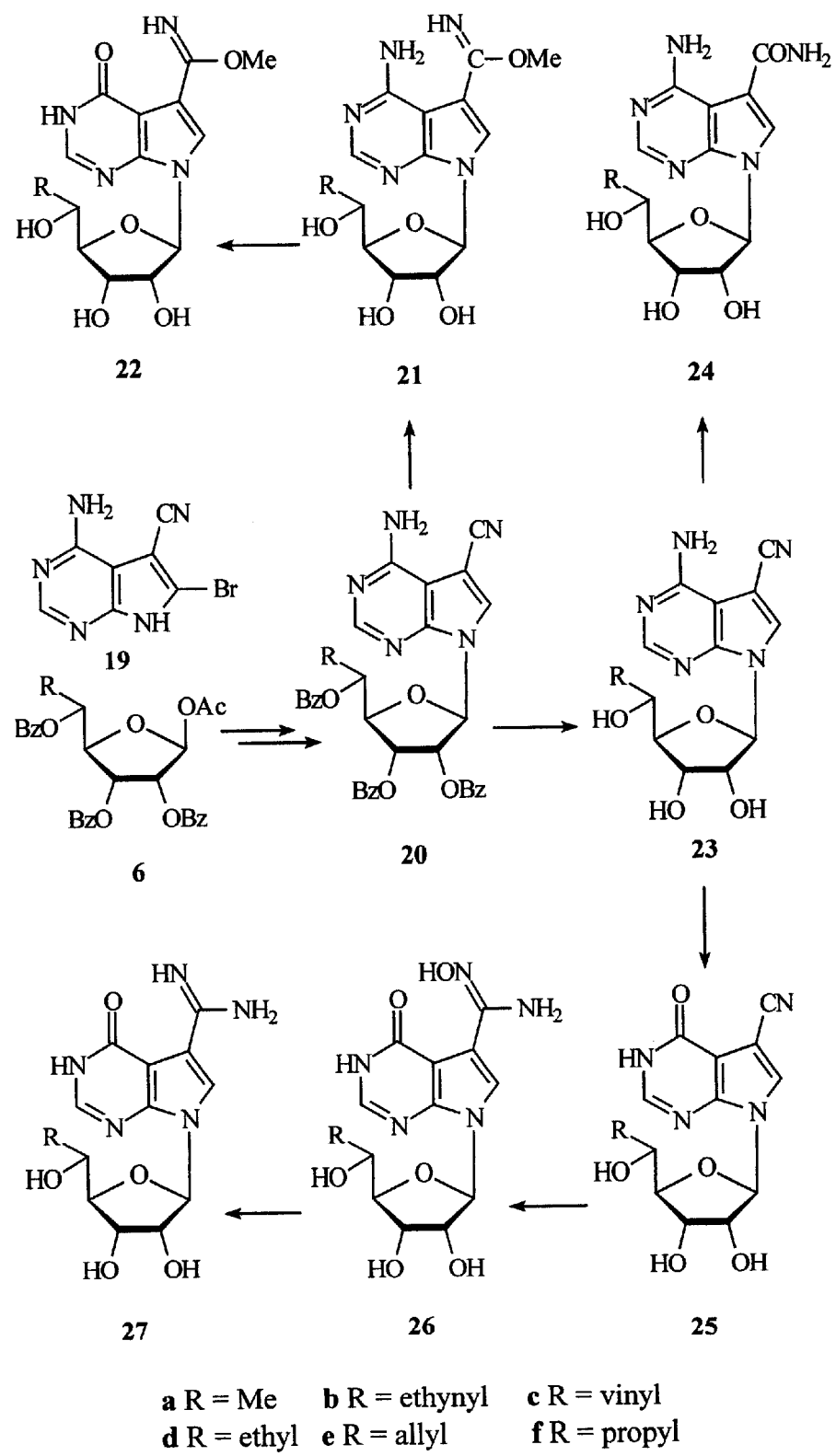
FIG. 4 is a fourth exemplary synthetic scheme of reactions included in the production of compounds according to the inventive subject matter.

As shown in FIG. 3, Compound 2 was converted to the sulfonate 16, which was subjected to nucleophilic replacement to give the configurationally inverted compound 17. Deprotection of the isopropylidene and the subsequent acetylation gave the tetraacetate 18. Condensation of the 5-C-substituted, protected ribofuranoses with nucleoside bases is depicted in FIG. 4. 5-Cyanopyrrolo[2,3-d]pyrimidine 19, prepared according to a published procedure (Tolman et al. J. Org. Chem. 1969, 91, 2102–2108), was converted to the trimethylsilyl derivative and then condensed with compound 6 in the presence of trimethylsilyl triflate by a similar procedure described for toyocamycin (Sharma et al. Nucleosides Nucleotides 1993, 12, 643–648). The resulting coupling product was subjected to debromination through hydrogenation to give compound 20. Treatment of 20 with ammonia in anhydrous methanol gave compounds 21 and 23. Compound 21 was oxidized to give compound 22. Compound 23 was converted to the carboxamide derivative 24. Compound 23 and 24 were oxidized to give compound 25. Treatment of compound 25 with hydroxyamine yielded compound 26, which was hydrogenated over Raney Nickel to give 27. Alternatively, compound 27 was also prepared by heating compound 25 with ammonia in a pressured bomb.

Synthesis of C4'-modified pyrrolo[2,3-d]pyrimidine nucleoside analogs

Figure 5:
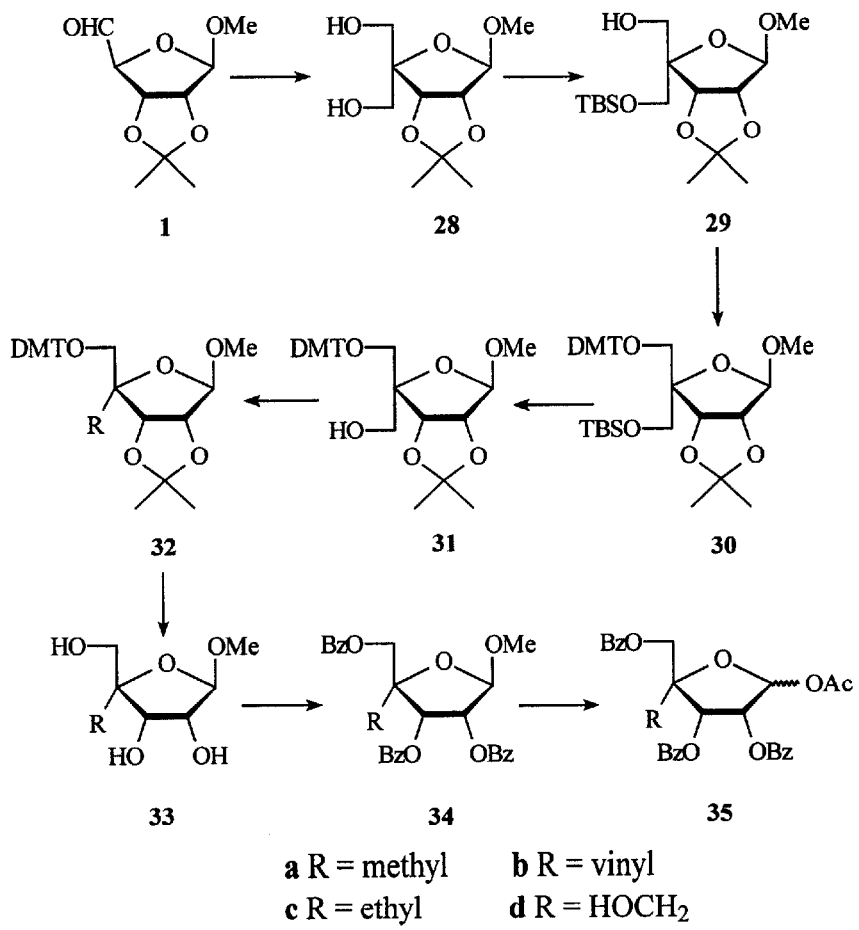
FIG. 5 is a fifth exemplary synthetic scheme of reactions included in the production of compounds according to the inventive subject matter.

In FIG. 5, compound 1 was treated with formaldehyde in aqueous sodium hydroxide to give 4'-hydroxymethyl derivative 28, which was selectively protected to afford compound 29. The subsequent protection with DMT and removal of TBS gave compound 31, which can be converted to a variety of substituents. The 4-C-substituted derivatives subjected to similar transformations as 5-C-substituted ribofuranoses (scheme 1) can be converted to compound 35, which is used for condensation with nucleoside bases.

Figure 6:
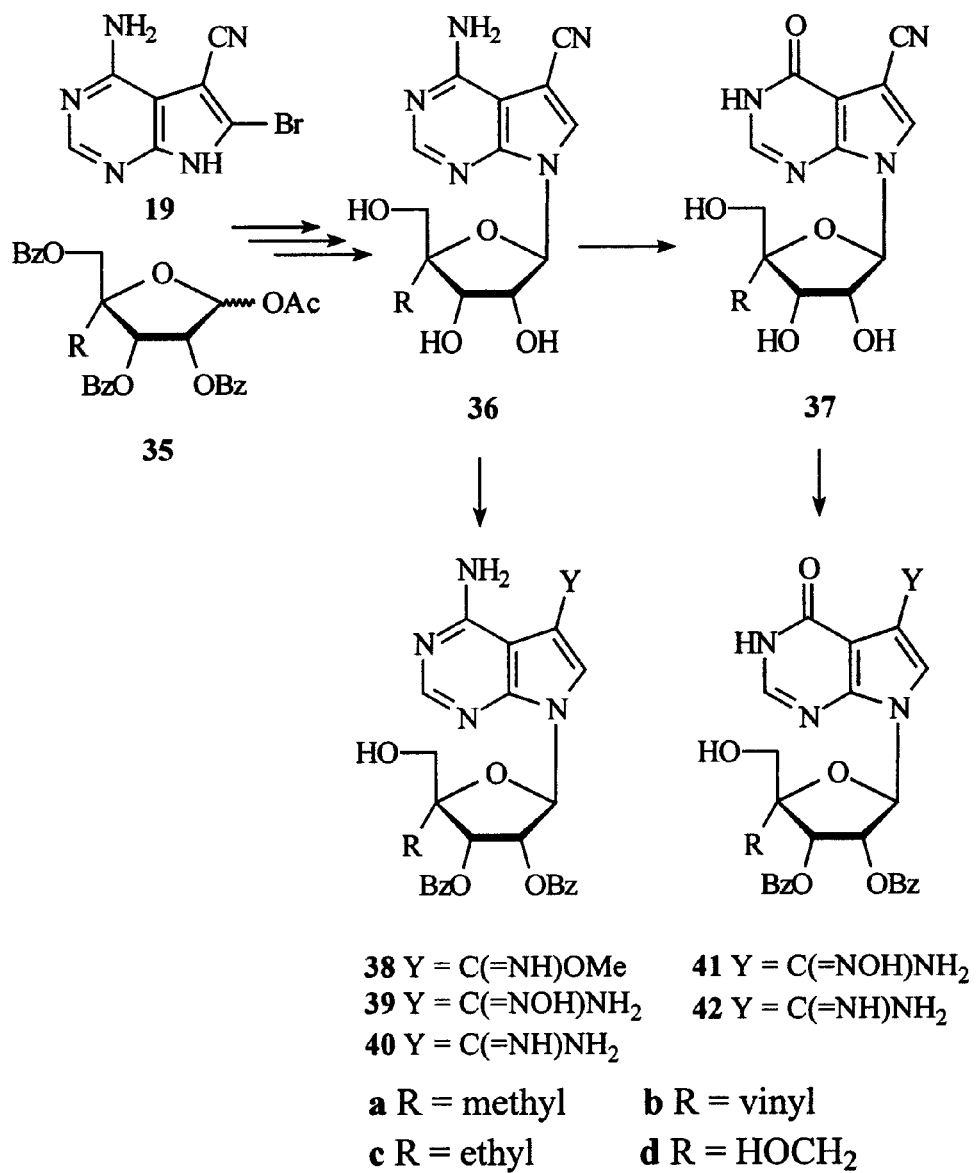
FIG. 6 is a sixth exemplary synthetic scheme of reactions included in the production of compounds according to the inventive subject matter.

Similar to the C5'-substituted pyrrolopyrimidine nucleoiside analogs, the 4'-substituted analogs 36 can be obtained by condensation of compound 35 with compound 19 as depicted in FIG. 6. The subsequent transformations can give the 4'-C-substituted pyrrolopyrimidine nucleoside 37–42.

Synthesis of 2'-modified, and other pyrrolo[2,3-d]pyrimidine nucleoside analogs

Figure 7:
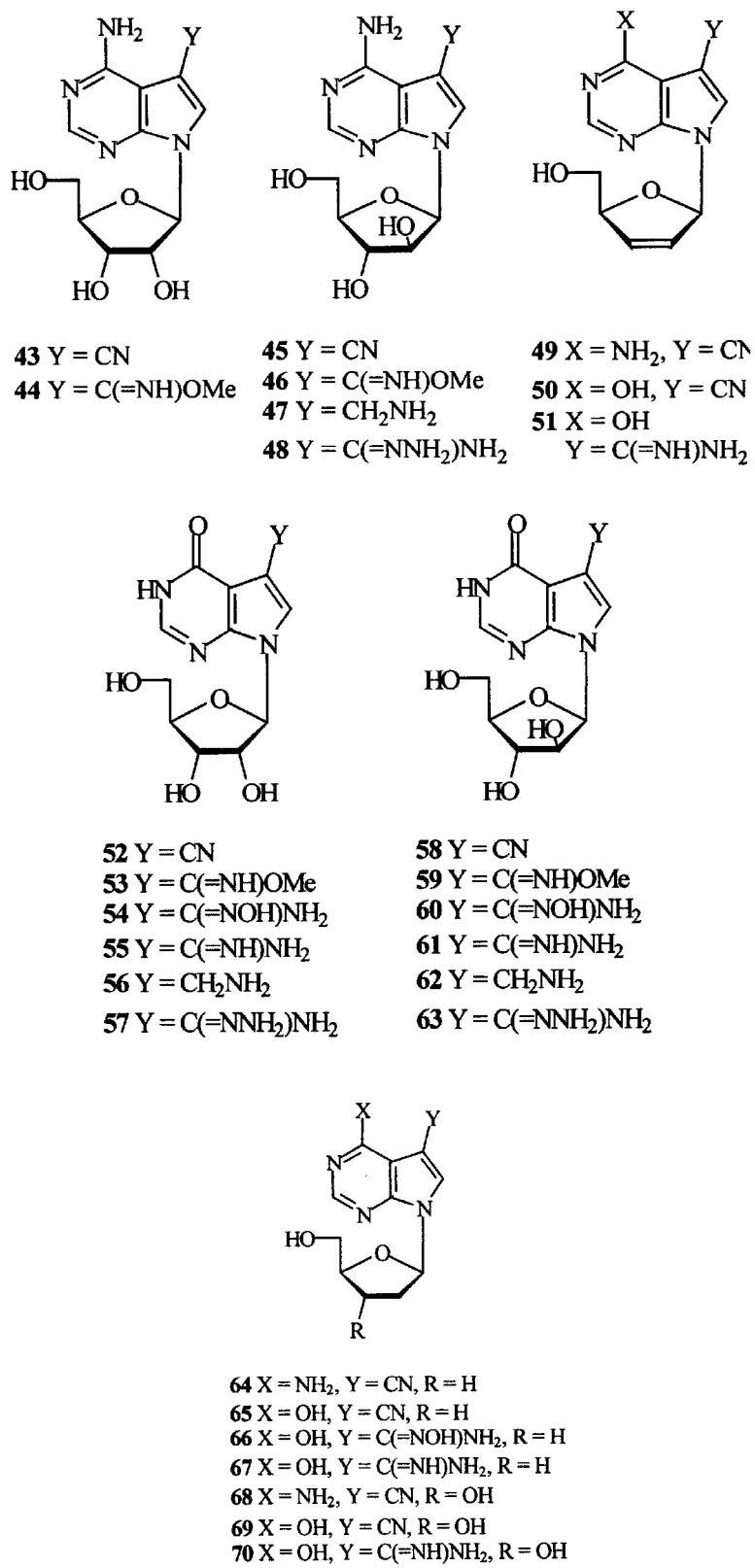
FIG. 7 depicts exemplary compounds according to the inventive subject matter.

The following pyrrolopyrimidine nucleoside analogs were prepared for biological testing, some of which were published (indicated as known compounds), and are shown in FIG. 7. The known compounds 43, 44, 52–55, and 57 were prepared according to a published procedure (Hinshaw et al. J. Org. Chem. 1970, 92, 236–241). Compound 56 was prepared by hydrogenation of compound 52. The known compound 49 (Krawczyk et al. Nucleosides Nucleotides 1989, 8, 97–115) was treated with sodium nitrite to give compound 50. The known compounds 45 and 48 were prepared according to a published procedure (Ramasamy et al. J. Heterocyclic Chem. 1988, 25, 1043–1046). Compound 45 was treated with ammonia-methanol to give compound 46 and hydrogenated to give compound 47. Compounds 58–63 were prepared from compound 45 by similar procedures used for compounds 52–57. The known compound 64 (Krawczyk et al. Nucleosides Nucleotides 1989, 8, 97–115) was converted to compounds 65–67. The known compound 68 (Ramasamy et al. Tetrahedron 1986, 42, 5869–5878) was converted to compounds 69 and 70.

Synthesis of Compounds According to Formula III
7-β-D-ribofuranosyl-4-oxopyrrolo[2,3-d]pyrimidine-5-carboxamidine and the corresponding HCl salt were synthesized as described previously (Synthesis and cytokine modulation properties of pyrrolo[2,3-d]-4-pyrimidone nucleosides. *J Med Chem.* Jun. 29, 2000; 43(13):2566–74.). An exemplary synthetic route is outlined below.
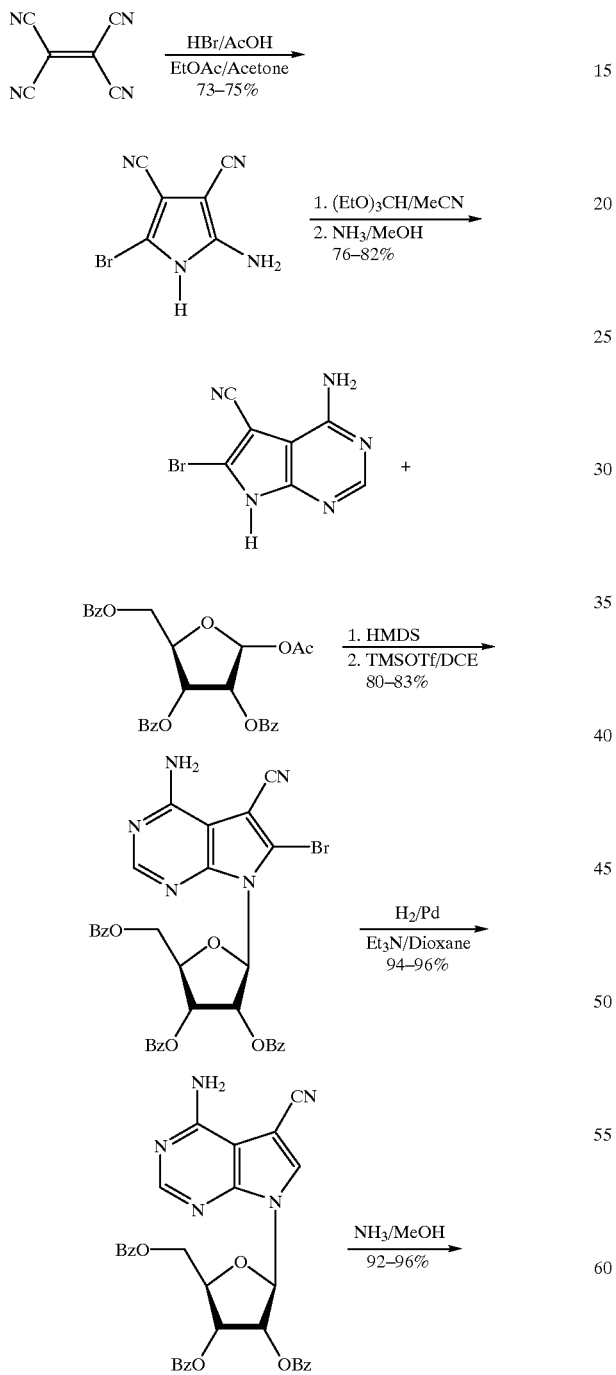
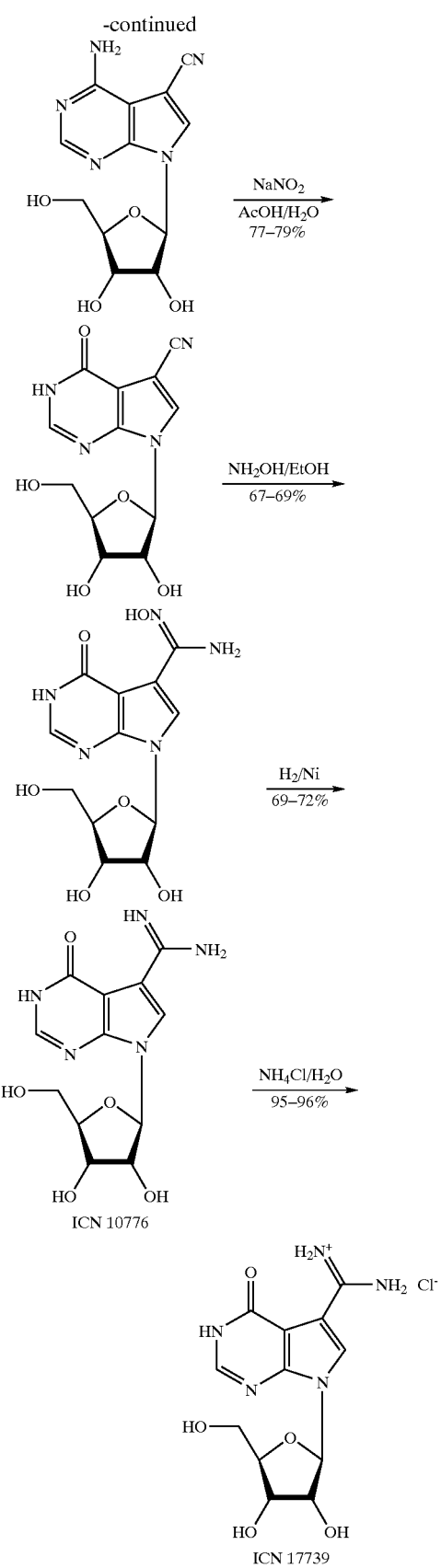

EXAMPLES

Synthesis of Exemplary Contemplated Compounds

The following protocols describe an exemplary synthesis of various compounds according to the inventive subject matter and are intended only to illustrate but not to limit the inventive concept presented herein.

Preparation of methyl 2,3-O-isopropylidene-5(R,S)-C-ethynyl-β-ribofuranoside (2b)

To a stirred solution of methyl 4-C,5-O-didehydro-2,3-O-isopropylidene-β-D-ribofuranosied (Jones et al. *Methods in Carbohydrate Chemistry* Vol 1, pp315–322 (1972), 4.00 g, 19.78 mmol) in anhydrous THF (20 mL) at −42° C. under argon was added dropwise ethynylmagnesium bromide (0.5 M in THF, 80 mL, 40 mmol). Upon addition, the resulting mixture was slowly warmed up to 0° C. (~90 min.). The reaction was quenched by adding ice (50 g)/water (50 mL) and the mixture was stirred for 30 min. After neutralization with 10% aq. acetic acid, the mixture was extracted with ethyl acetate twice. The combined organic layer was dried ($Na_2SO_4$) and concentrated. Chromatography on silica (ethyl acetate-hexanes 1:4) gave 3.48 g of the titled compound (R/S ratio 1:1) as a white solid. The following compounds were prepared in a similar fashion: Methyl 2,3-O-isopropylidene-5(R)-C-methyl-β-D-ribofuranoside (2a) was prepared from methyl 4-C,5-O-dihehydro-2,3-O-isopropylidene-β-D-ribofuranoside and ethylmagnesium bromide. Methyl 2,3-O-isopropylidene-5(R)-C-vinyl-β-D-ribofuranoside (2c) was prepared from methyl 4-C,5-O-dihehydro-2,3-O-isopropylidene-β-D-ribofuranoside and vinylmagnesium bromide. Methyl 5(R)-C-allyl-2,3-O-isopropylidene-β-D-ribofuranoside (2d) was prepared from methyl 4-C,5-O-dihehydro-2,3-O-isopropylidene-β-D-ribofuranoside and allylmagnesium bromide.

Preparation of methyl 2,3-O-isoproplidene-5-O-methanesulfonyl-5(R)-C-methyl-β-D-ribofuranoside (16)

To a stirred solution of methyl 2,3-O-isopropylidene-5(R)-C-methyl-β-D-ribofuranoside (2a, 7.24 g, 33.17 mmol) in anhydrous pyridine (50 mL) at 0° C. was added methanesulfonyl chloride (3.1 mL, 39.92 mmol). The resulting mixture was stirred at room temperature for 1 h, cooled to 0° C., quenched by adding water (1.0 mL), and stirred at room temperature for 30 min. The solvent was evaporated and the residue was dissolved in ethyl acetate, washed with brine three times, dried ($Na_2SO_4$) and concentrated. Chromatography on silica (30% EtOAc in hexanes) gave 8.62 g of the titled compound 16 as a colorless syrup.

Preparation of methyl 2,3-O-isopropylidene-5-O-acetyl-5(S)-C-methyl-β-D ribofuranoside (17)

A stirred suspension of methyl 2,3-O-isopropylidene-5-O-methanesulfonyl-5(R)-C-methyl-β-D-ribofuranoside (16, 8.62 g, 29.1 mmol) and NaOAc (anhydrous, 3.5 g, 42.5 mmol) in anhydrous DMF (350 mL) was heated at 125° C. under argon for 4 days. The solvent was evaporated and the residue chromatographed on silica (25% EtOAc in hexanes) to give 4.0 g of the titled compound 17 as a white solid.

Preparation of methyl 2,3-O-isopropylidene-4-C-hydroxymethyl-β-D-ribofuranoside (28)

To a stirred solution of methyl 4-C,5-O-didehydro-2,3-O-isopropylidene-β-D-ribofuranoside 1 (20.22 g, 100 mmol) in dioxane (380 mL) at 0° C. was added dropwise formaldehyde (37% solution, 76 mL) and then 2 M NaOH (188 mL). The resulting reaction mixture was stirred at room temperature for 20 h, cooled to 0° C., neutralized (10% acetic acid), concentrated (~50%), and extracted with methylene chloride twice. The combined organic layer was dried ($Na_2SO_4$) and concentrated to dryness. Chromatography on silica (4% methanol in chloroform) gave 20.2 g of the titled compound 28 as a white solid.

Preparation of methyl 2,3-O-isopropylidene-5-deoxy-β-D-ribofuranoside (8)

To a stirred solution of methyl 2,3-O-isopropylidene-β-D-ribofuranoside (14.2 g, 70.0 mmol) in anhydrous pyridine (250 mL) at 10° C. was added in portions (over 30 min) p-toluenesulfonyl chloride (19.1 g, 100 mmol). The resulting mixture was stirred at room temperature for 18 h, cooled to 0° C., quenched by adding water (5.0 mL), and stirred at room temperature for 30 min. The solvent was evaporated. The residue was dissolved in ethyl acetate, washed with brine three times, dried ($Na_2SO_4$) and concentrated to dryness. Chromatography on silica (ethyl acetate-hexanes 1:3) gave 24.1 g of the titled compound as a white solid.

To a stirred suspension of $LiAlH_4$ (4.58 g, 120.5 mmol) in anhydrous diethyl ether (120 mL) was added methyl 2,3-O-isopropylidene-5-O-p-toluenesulfonyl-β-D-ribofuranoside (13.1 g, 36.55 mmol) in diethyl ether-toluene (2.5:1, 140 mL). The resulting mixture was refluxed for 22 h, cooled to room temperature, diluted with ethyl acetate (25 mL) quenched by adding water (5.0 mL). The solvent was evaporated. The residue was dissolved in ethyl acetate, washed with brine three times, dried ($Na_2SO_4$) and concentrated to dryness. Chromatography on silica (ethyl acetate hexanes 1:3) gave 3.58 g of the titled compound as a colorless liquid.

Preparation of methyl 5(R)-C-allyl-5-O-benzoyl-2,3-O-isopropylidene-β-D-ribofuranoside (3d)

To a stirred solution of methyl 5(R)-C-allyl-2,3-O-isoproplidene-β-D-ribofuranoside (4.49 g, 18.38 mmol) in anhydrous pyridine (40 mL) at 0° C. was added benzoyl chloride (2.7 mL, 23.0 mmol). The resulting mixture was stirred at room temperature for 18 h, cooled with ice, quenched by adding water (1 mL), and stirred at room temperature for 30 min. The solvent was evaporated and the residue was dissolved in ethyl acetate, washed with brine three times, dried ($Na_2SO_4$) and concentrated. Chromatography on silica (12% ethyl acetate in hexanes) gave 6.26 g of the titled compound 3d as a colorless syrup. The following compounds were prepared in a similar fashion: Methyl 5-O-benzoyl-5(R,S)-C-ethynyl-2,3-O-isoproplidene-β-D-ribofuranoside (3b, R/S ratio: 1:1) from methyl 5(R,S)-C-ethynyl-2,3-O-isoproplidene-β-D-ribofuranoside (2b). Methyl 4-C-benzoyloxymethyl-5-O-benzoyl-2,3-O-isoproplidene-β-D-ribofuranoside from methyl 2,3-O-isoproplidene-4-C-hydroxymethyl-β-D-ribofuranoside.

Preparation of methyl 5(R)-C-allyl-5-O-benzoyl-β-D-ribofuranoside (4d)

A solution of methyl 5(R)-C-allyl-5-O-benzoyl-2,3-O-isopropylidene-β-D-ribofuranoside (3d, 6.2 g, 17.8 mmol) in TFA-$H_2O$ mixture (9:1) was stirred at 0° C. for 90 min and concentrated to dryness at 0° C. The residue was dissolved in methanol-toluene mixture (20 mL, 1:1) and concentrated to dryness. Chromatography on silica (ethyl acetate-hexanes 1:1) gave 3.70 g of the titled compound 4d as a white solid. The following compounds were prepared in a similar fashion: Methyl 5-O-benzoyl-5(R,S)-C-ethynyl-β-D-ribofuranoside (4b, R/S ratio: 1:1) from methyl 5-O-benzoyl-5(R,S)-C-ethynyl-2,3-O-isopropylidene-β-D-ribofuranoside (3b). Methyl 5-O-benzoyl-4-C-benzoyloxymethyl-β-D-ribofuranoside from methyl 5-O-benzoyl-4-C-benzoyloxymethyl-2,3-O-isopropylidene-β-D-ribofuranoside.

Preparation of methyl 5(R)-C-allyl-2,3,5-tri-O-benzoyl-β-D-ribofuranoside (5d)

To a stirred solution of methyl 5(R)-C-allyl-5-O-benzoyl-β-D-ribofuranoside (4d, 3.60 mg, 11.68 mmol) in anhydrous pyridine (80 mL) at 0° C. was added benzoyl chloride (3.0 mL, 25.84 mmol). The resulting mixture was stirred at room temperature for 18 h, cooled with ice, quenched by adding water (1 mL), then stirred at room temperature for 30 min. The mixture was concentrated, diluted with ethyl acetate, washed with brine three times, dried ($Na_2SO_4$) and concentrated to dryness. Chromatography on silica (15% ethyl acetate in hexanes) gave 5.3 g of the titled compound 5d as a colorless syrup. The following compounds were prepared in a similar fashion: Methyl 5(R,S)-C-ethynyl-2,3,5-tri-O-benzoyl-β-D-ribofuranoside (5b, R/S ratio: 1:1) from methyl 5-O-benzolyl-5(R,S)-C-ethynyl-β-D-ribofuranoside (4b). Methyl 4-C-benzoyloxomethyl-2,3,5-tri-O-benzoyl-β-D-ribofuranoside from methyl 4-C-benzoyloxymethyl-5-O-benzoyl-β-D-ribofuranoside.

Preparation of 1-O-methyl-2,3,5-tri-O-benzoyl-5(R)-C-vinyl-β-D-ribofuranose (5c)

A solution of methyl 2,3-O-isopropylidene-5(R)-C-vinyl-β-D-ribofuranosise (2c, 1.0 g, 4.3 mmol) in a mixture of trifluoroacetic acid and water (9:1, v/v, 11 mL) was stirred at 0° C. for 30 min and concentrated to dryness. The residue was dissolved in methanol and concentrated to dryness (3 times), then dissolved in pyridine and evaporated, and finally was dissolved in anhydrous pyridine (11 mL). To this solution was added benzoyl chloride (1.9 mL, 16 mmol). The reaction mixture was stirred at 25° C. for 16 h and poured into ice water (20 mL). The mixture was extracted with dichloromethane (20 mL) and the organic layer was dried over sodium sulfate, and concentrated to dryness. The residue was chromatographed on silica (0–5% ethyl acetate in dichloromethane) to give 1.0 g of the titled compound 5c as a syrup.

Preparation of 1-O-acetyl-2,3,5-tri-O-benzoyl-5(R)-C-allyl-D-ribofuranose (6d)

To a stirred solution of methyl 5(R)-C-allyl-2,3,5-tri-O-benzolyl-β-D-ribofuranoside (5d, 4.0 g, 7.74 mmol) in acetic acid (14 mL) and acetic anhydride (1.75 mL, 18.36 mmol) at 0° C. was added concentrated sulfuric acid (200 μL, 3.79 mmol in 4.0 mL of acetic acid). The resulting mixture was stirred at room temperature for 20 h, cooled to 0° C., diluted with cold ethyl acetate, washed with water, 5% aq. $NaHCO_3$ and then brine, dried ($Na_2SO_4$), and concentrated. Chromatography on silica (ethyl acetate-hexanes 1:4) gave 2.82 g of the titled compound 6d (α/βratio: 1:2) as a colorless foam. The following compounds were prepared in a similar fashion: 1-O-Acetyl-5(R,S)-C-ethynyl-2,3,5-tri-O-benzolyl-β-D-ribofuranose (6b, R/S ratio: 1:1 and α/ratio: 1:2) from methyl 5(R,S)-C-ethynyl-2,3,5-tri-O-benzolyl-β-D-ribofuranoside (5b). 1-O-Acethyl-4-C-benzoyloxymethyl-2,3,5-tri-O-benzoyl-D-ribofuranoside (α/βratio: 1:3) from methyl 4-C-benzoyloxymethyl-2,3,5-tri-O-benzoyl-β-D-ribofuranoside. 5(R)-C-Methyl-1,2,3,5-tetra-O-acetyl-β-D-ribofuranose from methyl 2,3-O-isopropylidene-5(R)-C-methyl-β-D-ribofuranoside. 1,2,3,5-Tetra-O-acetyl-5(S)-C-methyl-D-ribofuranoside 6a from methyl 5-O-acetyl-2,3-O-isopropylidene-5(R)-C-methyl-β-D-ribofuranoside. 5-deoxy-1,2,3-tri-O-acetyl-D-ribofuranose 9 from methyl 5-O-acetyl-2,3-O-isopropylidene-β-D-ribofuranoside. 1-O-Acetyl-2,3,5-tri-O-benzoyl-5(R)-C-vinyl-β-D-ribofuranoside 6c from methyl 2,3,5-tri-O-benzoyl-5(R)-C-vinyl-β-D-ribofuranoside.

Preparation of 4-amino-6-bromo-5-cyano-7-(2,3,5-tri-O-benzoyl-5(R)-C-allyl-β-D-ribofuranosyl) pyrrolo[2,3-d]pyrimidine A suspension of 4-amino-6-bromo-5-cyanopyrrolo[2,3-d] pyrimidine (Tolman et al. J. Org. Chem. 1969, 91, 2102–2108, 1.05 g, 4.41 mmol) and ammonium sulfate (50 mg) in HMDS (75 mL) and anhydrous m-xylene (25 mL) was refluxed under argon for 18 h. Solvents were evaporated and the residue was dried under vacuum. The residue was dissolved in anhydrous 1,2-dichloroethane (80 mL) and mixed with 1-O-acetyl-2,3,5-tri-O-benzoyl-5(R)-C-allyl-D-ribofuranose (2.00 g, 3.67 mmol). Under cooling with ice, TMSOTf (1.3 mL, 7.30 mmol in 5 mL of anhydrous 1,2-dichloroethane) was added. The mixture under argon was stirred at room temperature for 30 min, then refluxed for 90 h, quenched by pouring it (cold) onto ice/$NaHCO_3$ (50 mL), and filtered. The organic layer was separated, dried ($Na_2SO_4$), and concentrated. Chromatography on silica (EtOAc-hexanes 2:3) gave 1.81 g of the titled compound as a colorless solid. The following compounds were prepared in a similar fashion: 4-Amino-6-bromo-5-cyano-7-(2,3,5-tri-O-benzoyl-5(R,S)-C-ethynyl-β-D-ribofuranosyl)pyrrolo [2,3-d]pyrimidine (R/S ratio: 1:1) was prepared from 1-O-acethyl-2,3,5-tri-O-benzolyl-5(R,S)-C-ethynyl-D-ribofuranose and 4-amino-6-bromo-5-cyanopyrrolo[2,3-d] pyrimidine. 4-amino-6-bromo-5-cyano-7-(4-enzoyloxomethyl-2,3,5-tri-O-benzoyl-β-D-ribofuranosyl) pyrrolo[2,3-d]pyrimidine was prepared from 1-O-acetyl-4-benzoyloxymethyl-2,3,5-tri-O-benzoyl-D-ribofuranose and 4-amino-6-bromo-5-cyano-pyrrolo[2,3-d]pyrimidine. 4-Amino-6-bromo-5-cyano-7-(1,2,3,5-tetra-O-acetyl-5(R)-C-methyl-β-D-ribofuranosyl)pyrrolo[2,3-d]pyrimidine was prepared from 1,2,3,5-tetra-O-acetyl-5(R)-C-methyl-D-ribofuranose and 4-amino-6-bromo-5-cyanopyrrolo[2,3-d]pyrimidine. 4-Amino-6-bromo-5-cyano-7-(1,2,3,5-tetra-O-acetyl-5(S)-C-methyl-β-D-isbofuranosyl)pyrrolo[2,3-d] pyrimidine was prepared from 1,2,3,5-tetra-O-acethyl-5(S)-C-methyl-D-ribofuranoside and 4-amino-6-bromo-5-cyanopyrrolo[2,3-d]pyrimidine. 4-Amino-6-bromo-5-cyano-7-(2,3-di-O-acetyl-5-deoxy-β-D-ribofuranosyl) pyrrolo-[2,3-d]pyrimidine was prepared from 1,2,3-tri-O-acetyl-5-deoxy-D-ribofuranose and 4-amino-6-bromo-5-cyanopyrrolo[2,3-d]pyrimidine. 4-Amino-6-bromo-5-cyano-7-(2,3,5-tri-O-benzoyl-5(R)-C-vinyl-β-D-ribofuranosyl)pyrrolo[2,3-d]pyrimidine was prepared from 1-O-acetyl-2,3,5-tri-O-benzoyl-5(R)-C-vinyl-β-D-ribofuranose and 4-amino-6-bromo-5-cyanopyrrolo-[2,3-d] pyrimidine.

Preparation of 4-amino-5-cyano-7-(2,3,5-tri-O-benzoyl-5(R)-C-allyl-β-D-ribofuranosyl)pyrrolo[2,3-d]pyrimidine (20e)

To a solution of 4-amino-6-bromo-5-cyano-7-(2,3,5-tri-O-benzoyl-5(R)-C-allyl-β-D-ribofuranosyl)pyrrol[2,3-d] pyrimidine (738 mg 1.0 mmol) in acetic acid (25 mL) was added zinc dust (1.04 g, 16.0 mmol) in two portions (one hour apart). The reaction mixture was stirred at room temperature for 20 h and filtered. The filtrate was evaporated to dryness and the residue chromatographed on silica (ethyl acetate-hexanes 1:1) to give 450 mg of titled compound 20e as a colorless foam. The following compounds were prepared in a similar fashion: 4-Amino-5-cyano-7-(2,3,5-tri-O-benzoyl-5(R,S)-C-ethynyl-β-D-ribofuranosyl)pyrrolo[2,3-d]pyrimidine (R/S ratio: 1:1) 20b from 4-amino-6-bromo-5-cyano-7-(2,3,5-tri-O-benzoyl-5(R,S)-C-ethynyl-β-D-ribofuranosyl)pyrrolo[2,3-d]pyrimidine. 4-Amino-5-cyano-7-(2,3,5-tri-O-benzoyl-5(R)-C-vinyl-β-D-ribofuranosyl)pyrrolo[2,3-d]pyrimidine 20c from 4-amino-6-bromo-5-cyano-7-(2,3,5-tri-O-benzoyl-5(R)-C-vinyl-β-D-ribofuranosyl)pyrrolo[2,3-d]pyrimidine.

Preparation of 4-amino-5-cyano-7-(2,3,5-tri-O-benzoyl-5(R)-C-propyl-β-D-ribofuranosyl)pyrrolo[2,3-d]pyrimidine (20f)

A suspension of 4-amino-6-bromo-5-cyano-7-(2,3,5-tri-O-benzoyl-5(R)-C-allyl-β-D-ribofuranosyl)pyrrolo[2,3-d]pyrimidine (400 mg, 0.54 mmol) and 10% Pd/C (100 mg, ~50% water) in dioxane (50 mL) and triethylamine (0.5 mL) was shaken in hydrogenation apparatus ($H_2$, 20 psi) for 4 h. The catalyst was filtered and washed (dioxane). The combined filtrate was concentrated and the residue chromatographed on silica (ethyl acetatehexanes 1:1) to give 340 mg of the titled compound 20f as a colorless foam. The following compounds were prepared in a similar fashion: 4-Amino-5-cyano-7-(2,3,5-tri-O-benzoyl-5(R,S)-C-ethyl-β-D-ribofuranosyl)pyrrolo[2,3-d]pyrimidine (R/S ratio: 1:1) 20d from 4-amino-6-bromo-5-cyano-7-(2,3,5-tri-O-benzoyl-5(R,S)-C-ethynyl-β-D-ribofuranosyl)pyrrolo[2,3-d]pyrimidine. 4-Amino-5-cyano-7-(4-benzoyloxomethyl-2,3,5-tri-O-benzoyl-β-D-ribofuranosyl)pyrrolo[2,3-d]pyrimidine from 4-amino-6-bromo-7-cyano-7-(4-benzoyloxomethyl-2,3,5-tri-O-benzoyl-β-D-ribofuranosyl)pyrrolo[2,3-d]pyrimidine. 4-Amino-5-cyano-7-(1,2,3,5-tetra-O-acethyl-5(R)-C-methyl-β-D-ribofuranosyl)pyrrolo-[2,3-d]pyrimidine 20a from 4-Amino-6-bromo-5-cyano-7-(1,2,3,5-tetra-O-acethyl-5(R)-C-methyl-β-D-ribofuranosyl)pyrrolo[2,3-d]pyrimidine. 4-Amino-5-cyano-7-(1,2,3,5-tetra-O-acetyl-5(S)-C-methyl-β-D-ribofuranosyl)pyrrolo[2,3-d]pyrimidine 20a from 4-Amino-6-bromo-5-cyano-7-(1,2,3,5-tetra-O-acethyl-5(S)-C-methyl-β-D-ribofuranosyl)pyrrolo-[2,3-d]pyrimidine. 4-Amino-5-cyano-7-(1,2,3-tri-O-acethyl-5-deoxy-β-D-ribofuranosyl)pyrrolo[2,3-d]pyrimidine from 4-amino-6-bromo-5-cyano-7-(1,2,3-tri-O-acethyl-5-deoxi-β-D-ribofuranosyl)pyrrolo[2,3-d]pyrimidine. 4-Amino-5-cyano-7-(2,3-dideoxy-β-D-gliceropentofuranosyl)pyrrolo[2,3-d]pyrimidine was prepared from 4-amino-5-cyano-7-(2,3-dideoxy-β-D-pent-2-enofuranosyl)pyrrolo[2,3-d]pyrimidine.

Preparation of 4-amino-5-cyano-7-(5(R)-C-allyl-β-D-ribofuranosyl)pyrrolo-[2,3-d]pyrimidine (23e)

A solution of 4-amino-5-cyano-7-(2,3,5-tri-O-benzoyl-5(R)-C-allyl-β-D-ribofuranosyl)pyrrolo[2,3-d]pyrimidine (300 mg, 0.454 mmol) in methanol (40 mL) at 0° C. was saturated with ammonia. The solution stood at room temperature for 2 days. Solvent was evaporated and the residue together with NaOAc (anhydrous, 20 mg) was suspended in DMF (20 mL). The mixture was stirred under argon at 120° C. for 5 h. Solvent was evaporated. The residue was adsorbed onto silica gel and eluted from silica gel column (methanol-ethyl acetate 1:25) to give 145 mg of the titled compound as a colorless solid.

Before heating in DMF, the product contained two major compounds 21 and 23, which could be separated by chromatography on silica gel. Compounds 21 were prepared through this procedure. The following compounds were prepared in a similar fashion: 4-Amino-5-cyano-7-(5(R)-C-propyl-β-D-ribofuranosyl)pyrrolo[2,3-d]pyrimidine 23f from 4-amino-5-cyano-7-(2,3,5-tri-O-benzoyl-5(R)-C-propyl-β-D-ribofuranosyl)-pyrrolo-[2,3-d]pyrimidine. 4-Amino-5-cyano-7-(5(RS)-C-ethynyl-β-D-ribofuranosyl)pyrrolo-[2,3-d]pyrimidine (R-S ratio: 1:1) 23b from 4-amino-5-cyano-7-(2,3,5-tri-O-benzoyl-5(R,S)-C-ethynyl-β-D-ribofuranosyl)pyrrolo-[2,3-d]pyrimidine. 4-Amino-5-cyano-7-(5(R,S)-C-ethyl-β-D-ribofuranosyl)pyrrolo[2,3-d]pyrimidine (R-S ratio: 1:1) 23d from 4-amino-5-cyano-7-(2,3,5-tri-O-benzoyl-5(R,S)-C-ethyl-β-D-ribofuranosyl)pyrrolo-[2,3-d]pyrimidine. 4-Amino-5-cyano-7-(4-hydroxymethyl-β-D-ribofuranosyl)pyrrolo-[2,3-d]pyrimidine 33d from 4-Amino-5-cyano-7-(4-benzoyloxomethyl-2,3,5-tri-O-benzoyl-β-D-ribofuranosyl)pyrrolo[2,3-d]pyrimidine. 4-Amino-5-cyano-7-(5(R)-C-methyl-β-D-ribofuranosyl)pyrrolo[2,3-d]pyrimidine 23a(5'-R) from 4-amino-5-cyano-7-(1,2,3,5-tetra-O-acethyl-5(R)-C-methyl-β-D-ribofuranosyl)pyrrolo[2,3-d]pyrimidine. 4-Amino-5-cyano-7-(5(S)-C-methyl-β-D-ribofuranosyl)pyrrolo[2,3-d]pyrimidine 23a(5'-S) from 4-amino-5-cyano-7-(1,2,3,5-tetra-O-acethyl-5(S)-C-methyl-β-D-ribofuranosyl)pyrrolo-[2,3-d]pyrimidine. 4-Amino-5-cyano-7-(5-deoxy-β-D-ribofuranosyl)pyrrolo-[2,3-d]pyrimidine 10 from 4-amino-5-cyano-7-(1,2,3-tri-O-acethyl-5-deoxi-β-D-ribofuranosyl)pyrrolo[2,3-d]pyrimidine. 4-Amino-5-cyano-7-(5(R)-C-vinyl-β-D-ribofuranosyl)pyrrolo[2,3-d]pyrimidine 23c from 4-amino-5-cyano-7-(2,3,5-tri-O-benzoyl-5(R)-C-vinyl-β-D-ribofuranosyl)pyrrolo-[2,3-d]pyrimidine.

Preparation of 4-amino-5-cyano-7-(2,3-di-O-methanesulfonyl-5-O-tert-butyldiphenylsilyl-β-D-ribofuranosyl)pyrrolo[2,3-d]pyrimidine To a stirred solution of toyocamicin 43 (5.83 g, 20.0 mmol) in anhydrous pyridine (100 mL) at 0° C. was added tert-butylchlorodiphenylsilane (6.2 mL, 24.0 mmol). The resulting mixture was stirred at room temperature for 18 h and then cooled to 0° C., and methanesulfonyl chloride (3.4 mL, 44.0 mmol) was added. The resulting mixture was stirred at room temperature for 2 h, cooled with ice, quenched by adding water (2 mL), and stirred at room temperature for 30 min. The solvent was evaporated. The residue was dissolved in ethyl acetate, washed with brine three times, dried ($Na_2SO_4$) and concentrated. Chromatography on silica (ethyl acetatehexanes 3:2) gave 8.41 g of the titled compound as a colorless solid.

Preparation of 4-amino-5-cyano-7-(5-O-tert-butyldiphenylsilyl-2,3-didehydro-2,3-dideoxy-β-D-ribofuranosyl)pyrrolo[2,3-d]pyrimidine Tellurium powder (200 mesh, 640 mg 5.0 mmol) under argon was sealed, mixed with lithium triethylborohydrate (1.0 M in THF, 11.25 mL, 11.25 mmol). The mixture was stirred at room temperature for 6 h and then cooled to 5° C., and 4-amino-5-cyano-7-(2,3-di-O-methanesulfonyl-5-O-tert-butyldiphenylsilyl-β-D-ribofuranosyl)pyrrolo[2,3-d]pyrimidine (1.40 g, 2.09 mmol) in THF (12 mL) was added. The resulting mixture was stirred at room temperature for 18 h, cooled with ice, quenched by adding water (0° C., 5 mL), and stirred at room temperature for 30 min. Solvent was evaporated and the residue extracted with ethyl acetate. The extracts were concentrated and the residue chromatographed on silica (15% ethyl acetate in hexanes) to give 640 mg of the titled compound as a colorless foam.

Preparation of 4-amino-5-cyano-7-(2,3-didehydro-2, 3-dideoxy-β-D-ribofuranosyl)-pyrrolo[2,3-d] pyrimidine (49)

To a stirred solution of 4-amino-5-cyano-7-(5-O-tert-butyldiphenylsilyl-2,3-didehydro-2,3-dideoxy-β-D-ribofuranosyl)pyrrolo[2,3-d]pyrimidine (2.55 g, 5.32 mmol) in anhydrous THF (100 mL) at 5° C. was added terabutylammonium fluoride (1.0 M in THF, 6.6 mL). The resulting mixture was stirred at room temperature for 3 h and concentrated. Chromatography on silica (6% methanol in ethyl acetate) gave 1.09 g of the titled compound 49 as a colorless solid.

Preparation of 5-cyano-7-(5(R)-C-methyl-β-D-ribofuranosyl)pyrrolo[2,3-d]-4-pyrimidone (25a)

To a stirred solution of 4-amino-5-cyano-7-(5(R)-C-methyl-β-D-ribofuranosyl)-pyrrolo[2,3-d]pyrimidine (306 mg, 1.0 mmol) in water (30 mL) and acetic acid (2.0 mL) at 55° C. was added in portions sodium nitrite (590 mg, 8.55 mmol). The resulting mixture was stirred at 70° C. for 3 h and more sodium nitrite (300 mg, 4.30 mmol) was added. The mixture was stirred at same temperature for additional 18 h. Solvent was evaporated and the residue chromatographed on silica (12% methanol in methylene chloride) to give 210 mg of the titled compound 25a(5'-R) as a colorless solid. Similarly, the following compounds were prepared: 4-Amino-5-cyano-7-(5(S)-C-methyl-β-D-ribofuranosyl) pyrrolo[2,3-d]-4-pyrimidone 25a(5'-S) from 4-amino-5-cyano-7-(5(S)-C-methyl-β-D-ribofuranosyl)-pyrrolo[2,3-] pyrimidine. 4-Amino-5-cyano-7-(β-D-arabinofuranosyl) pyrrolo[2,3-d]-4-pyrimidone 58 from 4-amino-5-cyano-7-(5-deoxi-β-D-arabinofuranosy)pyrrolo[2,3-d]pyrimidine. 4-Amino-5-cyano-7-(5-deoxy-β-D-ribofuranosyl)pyrrolo[2, 3-d]-4-pyrimidone 11 from 4-amino-5-cyano-7-(5-deoxy-β-D-ribofuranosyl)pyrrolo[2,3-d]pyrimidine. 4-Amino-5-cyano-7-(2,3-dideoxy-2,3-didehydro-β-D-glycero-pentofuranosyl)pyrrolo[2,3-d]-4-pyrimidone 50 from 4-amino-5-cyano-7-(2,3-dideoxy-β-D-pent-2-enofuranosyl)pyrrolo-[2, 3-d]pyrimidine. 4-Amino-5-cyano-7-(2,3-dideoxy-β-D-glycero-pentofuranosyl)pyrrolo[2,3-d]-4-pyrimidone 65 from 4-amino-5-cyano-7-(2,3-dideoxy-β-D-glyceropentofuranosyl)pyrrolo[2,3-d]pyrimidine. 4-Amino-5-cyano-7-(2-deoxy-β-D-furanosyl)pyrrolo[2,3-d]-4-pyrimidone 69 from 4-amino-5-cyano-7-(2-deoxy-β-D-eritropentofuranosyl)pyrrolo[2,3-d]pyrimidine.

Preparation of 7-(5(R)-C-methyl-β-D-ribofuranosyl) pyrrolo[2,3-d]-4-pyrimidone-5-carboxamidoxime (24a)

A stirred suspension of 5-cyano-7-(5(R)-C-methyl-β-D-ribofuranosyl)pyrrolo[2,3-d]-4-pyrimidone (240 mg, 0.784 mmol), hydroxylamine hydrochloride (163 mg, 2.352 mmol), and potassim carbonate (162 mg, 1.176 mmol) in ethanol (50 mL) was refluxed under argon for 18 h. Preciptate was filtered and washed with warm ethanol. The filtrate was concentrated and the residue chromatographed on silica (20% methanol in methylene chloride) to give 170 mg of the titled compound 26a(5'-R) as a colorless solid. Similarly, the following compounds were prepared: 4-Amino-5-cyano-7-(β-D-arabinofuranosyl)pyrrolo[2,3-d]-4-pyrimidone-5-carboxamidoxime 60 from 4-amino-5-cyano-7-(5-deoxi-β-D-arabinofuranosy)-pyrrolo[2,3-d]-4-pyrimidone.
4-Amino-5-cyano-7-(5-deoxy-β-D-ribofuranosyl)pyrrolo [2,3-d]-4-pyrimidone-5-carboxamidoxime 13 from 4-amino-5-cyano-7-(5-deoxy-β-D-ribofuranosyl)pyrrolo[2, 3-d]-4-pyrimidone. 4-Amino-5-cyano-7-(2,3-didehydro-2, 3-dideoxy-β-D-ribofuranosyl)pyrrolo-[2,3-d]-4-pyrimidone-5-carboxamidoxime 51 from 4-amino-5-cyano-7-(2,3-didehydro-2,3-dideoxy-β-D-ribofuranosyl)pyrrolo[2, 3-d]-4-pyrimidone. 4-Amino-5-cyano-7-(2-deoxy-β-D-ribofuranosyl)pyrrolo[2,3-d]-4-pyrimidone-5-carboxamidoxime from 4-amino-5-cyano-7-(2-deoxy-β-D-ribofuranosyl)pyrrolo[2,3-d]-4-pyrimidone.

Preparation of 7-(5(R)-C-methyl-β-D-ribofuranosyl) pyrrolo[2,3-d]-4-pyrimidone-5-carboxamidine hydrochloride (27a)

A suspension of 7-(5(R)-C-methyl-β-D-ribofuranosyl) pyrrolo[2,3-d]-4-pyrimidone-5-carboxamidoxime (110 mg, 0.324 mmol), ammonium chloride (20 mg, 0.374 mmol), and Raney nickel (50% slurry in water, 200 mg) in water (75 mL) was shaken in a hydrogenation apparatus ($H_2$, 50 psi) at room temperature for 18 h. The catalyst was filtered and washed (warm water). The combined filtrate was concentrated and the product was recrystallized from methanol to give 100 mg of the titled compound 27a(5'-R) as a colorless solid. The following compounds were prepared in similar fashion: 4-Amino-5-cyano-7-(β-D-arabinofuranosyl) pyrrolo[2,3-d]-4-pyrimidone-5-carboxamidine hydrochloride 63 from 4-amino-5-cyano-7-(5-deoxi-β-D-arabinofuranosy)pyrrolo[2,3-d]-4-pyrimidone-5-carboxamidoxime. 4-Amino-5-cyano-7-(5-deoxy-β-D-ribofuranosyl)pyrrolo[2,3-d]-4-pyrimidone-5-carboxamidine hydrochloride 15 from 4-amino-5-cyano-7-(5-deoxi-β-D-ribofuranosyl)pyrrolo[2,3-d]-4-pyrimidone-5-carboxamidoxime. 4-Amino-5-cyano-7-(2-deoxy-β-D-ribofuranosyl)pyrrolo[2,3-d]-4-pyrimidone-5-carboxamidine hydrochloride 70 from 4-amino-5-cyano-7-(2-deoxy-β-D-ribofuranosyl)pyrrolo[2,3-d]-4-pyrimidone-5-carboxamidoxime.

Biological Effects

The following examples are provided to illustrate some of the biological effects of contemplated compounds. In particular, the experimental data indicate that contemplated compounds inhibit activation-induced IFNγ, IL-2 and TNFα secretion and T cell proliferation but enhanced IL-4 and IL-5 production in human T cells in a dose-dependent manner.

The biological effect mediated by contemplated compounds on peripheral T cells peaked at 48 h, was seen with stimulation either by PMA/ionomycin or PHA, was observed at cytokine protein and mRNA levels in normal individuals and rheumatoid arthritis patients, and enhanced the number of Type 2 while diminishing the number of Type 1 cytokine-producing cells.

Moreover the induction of a Type 2 cytokine bias by contemplated compounds was concurrent with a diminution in mRNA expression of inducible nitric oxide synthase, c-myc, IL-6 and IL-1b (suggesting an anti-inflammatory effect), and was more dramatic in the CD4+ population of human T cells. Furthermore contemplated compounds induced a Th2 cytokine bias in murine lymph node-derived Th1 cells in vitro, and (at 0.3 and 0.6 mg/kg) administered i.p. in BALB/c mice, inhibited two Type 1 cytokine-mediated acute inflammatory responses, contact hypersensitivity to dinitrofluorobenzene and Staphylococcal enterotoxin B-induced inflammatory responses.

These in vivo effects were associated with augmented IL-10 and decreased IEFNγmRNA expression in lymphoid organs. Collectively these data indicate that contemplated compounds can functionally induce a Th2 cytokine bias in vitro and in vivo.

Preparation of Human T-cells and Activation in vitro

Peripheral blood mononuclear cells were isolated from healthy donors by density gradient centrifugation followed by T cell enrichment using Lymphokwik (One Lambda, Canoga Park Calif.). Contaminating monocytes were removed by adherence to plastic. Purified T cells were >99% CD2+, <1% HLA-DR+ and <5% CD25+ and were maintained in RPMI-AP5 (RPMI1640 medium containing 5% autologous plasma, 1% L-glutamine, 1% penicillin/streptomycin and 0.05% 2-mercaptoethanol). For determination of cytokine protein levels, T-cells ($0.2 \times 10^6$ cells in a volume of 0.2 ml) were activated by the addition of 2 ng phorbol myristate acetate plus 0.1 mg ionomycin (PMA-ION, both from Calbiochem, San Diego, Calif.) and incubated in 96 well plates in the presence of 0 or 10 $\mu$M of various guanosine nucleosides for 48 h at 37° C. Following activation, supernatants were analyzed for cell-derived cytokine production.

Extracellular Cytokine Analyses.

Human cytokine levels were determined in cell supernatants, following appropriate dilution, using ELISA kits specific for IFN$\gamma$ and IL-4 (Biosource, Camarillo, Calif.). All ELISA results were expressed as pg/ml.

Effect of pyrrolo-[2,3,d]pyrimidine Nucleoside Analogs on Extracellular Cytokine Levels in Activated Human T Cells.

Figure 8A:
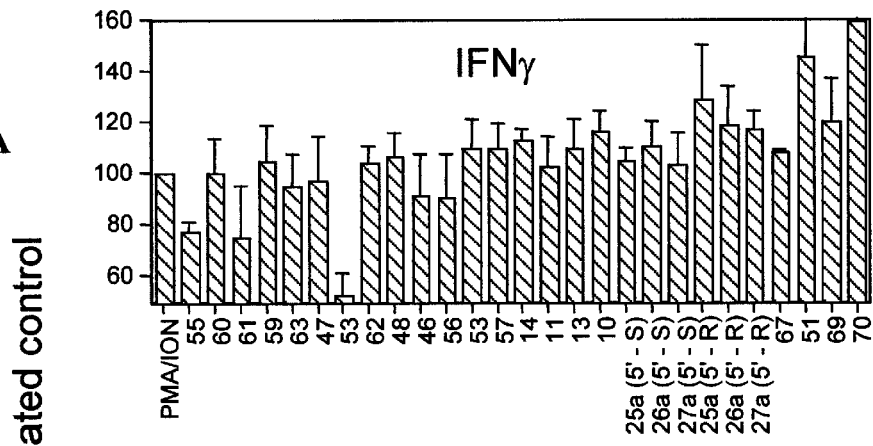
FIGS. 8A and 8B are graphs representing the effect of contemplated compounds on the expression of Type 1 and Type 2 cytokines, respectively.
Figure 8B:
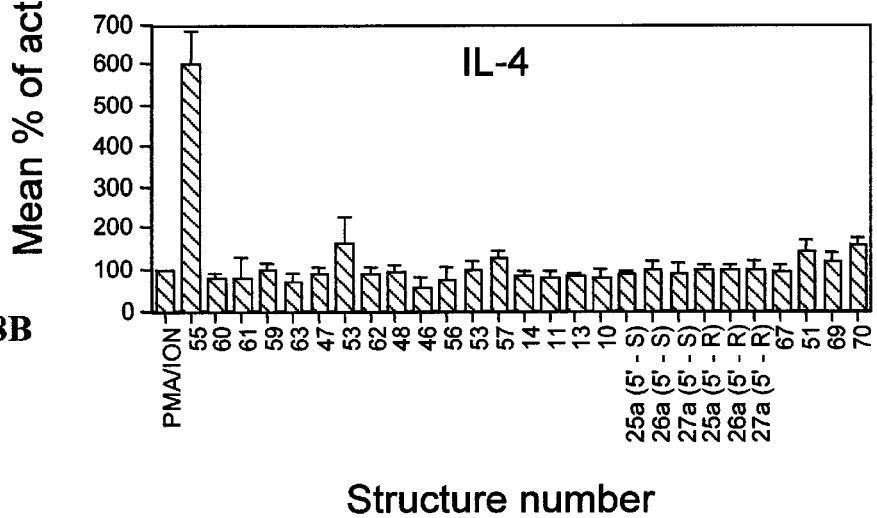

The effect of pyrrolo-[2,3-d]pyrimidine nucleoside analogs at 0 and 10 $\mu$M, on PMA/ionomycin stimulated T cell expression of the Type 1 cytokine, IFN$\gamma$, and the Type 2 cytokine, IL-4, is shown in FIGS. 8A and 8B for 5 individual human donors. Cytokine levels were determined in cell free supernatants by ELISA. The most potent effect was observed with 7-b-D-ribofuransyl-4-oxopyrrolo-[2,3-d]pyrimidine-5-carboxamidine. This compound enhanced activated IL-4 production by 498%±83 and suppressed IFN$\gamma$ by 43%±4 of the activated control levels of each cytokine. Data are shown as percentage of activated control calculated as the ratio of activated T cell cytokine level in the presence of test nucleosides over the cytokine level of untreated activated T cells×100%. Zero effect on cytokine levels by test nucleosides would give a percentage of activated control value of 100%. The absolute level (pg/ml±standard deviation) of PMA-ION-induced cytokine secretion was for IFN$\gamma$, 22954±3391; and for IL-4, 162±40. Resting levels were <30 pg/ml for all cytokines tested.

Cytotoxicity of the pyrrolo[2,3-d]pyrimidine Nucleoside Analogs in vitro

The pyrrolo[2,3-d]pyrimidine nucleoside analogs of the present invention are bioactive since they indicate some level of cytotoxicity in vitro. In these studies, the compounds tested were applied to cell culture of normal human fibroblasts, human Prostate cancer cells 81, human Melanoma cancer cells 140, Human Lung Cancer cells 177, and human Ovarian Cancer cells R and NR (all available from ATCC). In these experiments cells were plated at density of 2000 cells per 200 $\mu$l of medium per well (96-well plate). The compounds tested were applied to the wells once, at concentration range 0.78–100 $\mu$M, just after plating of cells. The colorimetric cytotoxicity assay MTS was performed after 72 hrs of treatment. EC50 was calculated based on readings collected and they are presented in FIG. 9. Several compounds indicate lack of cytotoxicity in concentration below 100 $\mu$M. In such cases EC50 is marked as >100. In other cases, EC50 indicates the concentration of the compound tested needed to damage 50% of cell population.

The pryrrolo[2,3-d]pyrimidine Nucleoside Analogs Inhibit DNA Synthesis in Cells Cultured in vitro in a Dose-dependent Manner Analogs of pyrrolo[2,3-d]pyrimidine nucleoside inhibit growth of human cells cultured in vitro as measured by the level of DNA. The experimental setup was the same as described above. The compounds were given once and DNA level was measured after 72 hrs. At that time, half of the medium was removed from culture wells and replaced by pure water. After that, the cells were transferred to −70° C. for at least 12 hrs. In the next step, cells were transferred back from −70° C. to room temperature and 1 $\mu$M of Hoechst 33342 was given to each well. After 2 hrs of incubation, the fluorescence signal (360–530 nm) was measured. According to this method, intensity of florescence is proportional to amount of DNA due to presence of DNA-Hoechst 33342 complex formed. The results are presented in FIG. 10. The numbers express fold of DNA amount increase compared to amount of DNA at the beginning of experiment (2 hrs after plating of cells). In the untreated prostate cancer cells and normal cells the DNA level increased 5.78 and 4.47 times, respectively, during 72 hrs of culture.

The Compounds 23a(5'-R) and 23a(5'-S) Inhibit Secretion of VEGF from Human Prostate Cancer in vitro.

Figure 11:
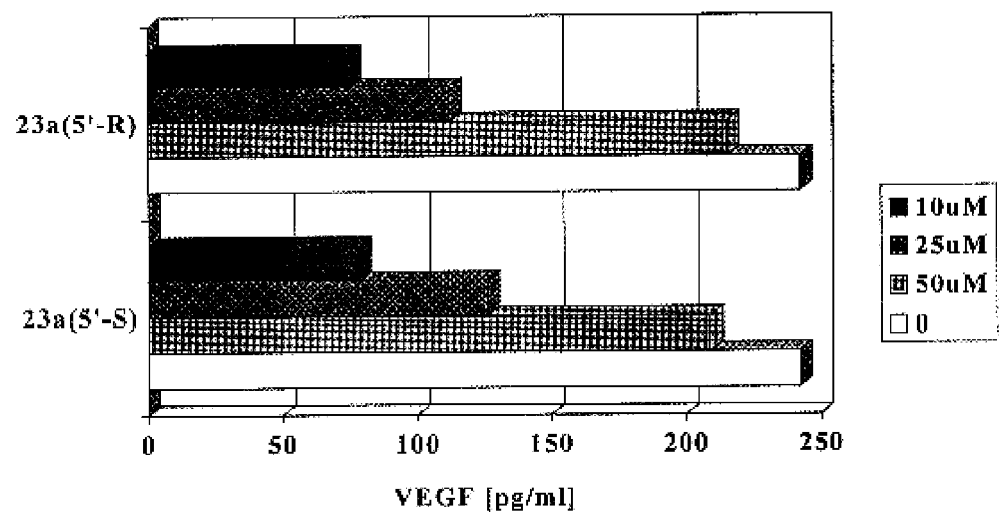
FIG. 11 is a graph depicting the inhibition of VEGF release from human prostate cancer cells upon treatment with compounds according to the inventive subject matter.

The compounds 23a(5'-R) and 23a(5'-S) are potent in inhibition of secretion of Vascular Endothelial Growth Factor (VEGF) from Human Prostate cancer cells, HTB81. VEGF is recognized as angiogenesis marker since this molecule is crucial for migration and growth of endothelial cells and microvessel formation in vivo. In order to prove this, $0.5 \times 10^5$ of the cells were plated in 5 ml of culture medium into a 10 cm diameter petri dish. The compounds were applied just after plating for 72 hrs. After that, the medium was collected and the level of VEGF was measured using VEGF Elisa Assay (R & D Systems) and expressed as pg of VEGF per ml of the medium. The results are presented in FIG. 11. According to these results, both compounds inhibit secretion of VEGF in a dose-dependent manner.

The Compounds 23a(5'-R) and 23a(5'-S) Inhibit Release of IL-8 from Human Prostate Cancer Cells Cultured in vitro.

Figure 12:
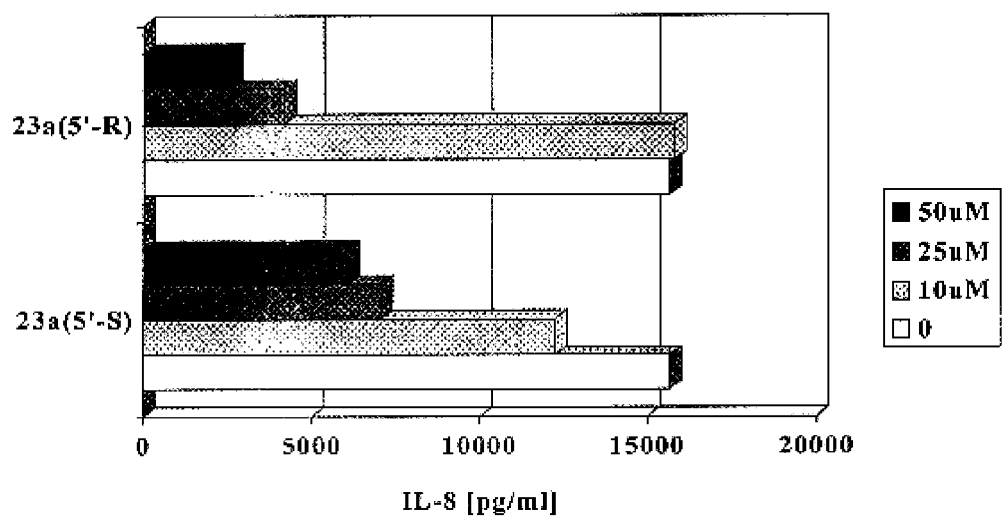
FIG. 12 is a graph depicting the inhibition of IL-8 release from human prostate cancer cells upon treatment with compounds according to the inventive subject matter.

The compound 23a(5'-R) and 23a(5'-S) indicate an inhibitory effect on secretion of Interleukin-8 (IL-8) from human prostate cancer cells, HTB81. IL-8 belongs to the class of chemo-attractant chemokines (type alpha), which are involved in inflammation processes due to attraction of neutrophils. Chemokines, in general, are known to be produced by various types of cancer. It is proven in several studies that inhibition of chemokine production by cancer cells is beneficial for the host. In order to prove the potency of these two compounds to inhibit IL-8 secretion from prostate cancer cells, prostate cancer cells HTB 81 were treated in vitro with compounds 23a in both the 5'-R and 5'-S configuration at concentrations indicated in the graph. The medium collected from the culture was analyzed for IL-8 level using IL-8 Elisa Assay from R&D Systems. According to the results collected, both compounds are able to inhibit secretion of IL-8 in a dose-dependent manner, as depicted in FIG. 12.

It should be appreciated, however, that the biological effects of contemplated compounds need not be limited to the particular effects as described above. In particular, it is contemplated that the compounds according to the inventive subject matter generally exhibit cytostatic effect in various hyperproliferative disorders, including localized and/or metastatic cancers (e.g, lymphomas and carcinomas), benign prostate hyperplasia, and keratoses. While the inventors found substantial biological effects on IL-4 (a Type 2 cytokine) and IFNγ (a Type 1 cytokine), it is generally contemplated that the compounds according to the inventive subject matter are biologically active in modulation of cytokines other than IL-4 and IFN-γ. It is especially contemplated that the compounds may increase or decrease the expression/secretion of a particular cytokine or set of cytokines. Therefore, it is contemplated that compounds according to the inventive subject matter may modulate the immune system of an organism such that a more pronounced Type 1 or Type 2 response may be achieved. Consequently, it is contemplated that the compounds according to the inventive subject matter may be effective to reduce the titer of a virus in a living system by either direct action as inhibitor of a viral polymerase and/or indirectly by activating the immune system to a particular humoral or cellular response. It is further contemplated that compounds according to the inventive subject matter may also be useful in reducing a response of an immune system towards an allo- or xenograft by reducing the severity of the cellular response towards the allo- or xenograft.

In further provided in vitro and in vivo examples, the experimental data indicate that contemplated compounds inhibit activation-induced IFNγ, IL-2 and TNFα secretion and T cell proliferation but enhanced IL-4 and IL-5 production in human T cells in a dose dependent manner.

The biological effect mediated by contemplated compounds on peripheral T cells peaked at 48 h, was seen with stimulation either by PMA/ionomycin or PHA, was observed at cytokine protein and mRNA levels in normal individuals and rheumatoid arthritis patients, and enhanced the number of Type 2 while diminishing the number of Type 1 cytokine-producing cells.

Moreover the induction of a Type 2 cytokine bias by contemplated compounds was concurrent with a diminution in mRNA expression of inducible nitric oxide synthase, c-myc, IL-6 and IL-1b (suggesting an anti-inflammatory effect), and was more dramatic in the CD4+ population of human T cells. Furthermore contemplated compounds induced a Th2 cytokine bias in murine lymph node-derived Th1 cells in vitro, and (at 0.3 and 0.6 mg/kg) administered i.p. in BALB/c mice, inhibited two Type 1 cytokine-mediated acute inflammatory responses, contact hypersensitivity to dinitrofluorobenzene and Staphylococcal enterotoxin B-induced inflammatory responses.

These in vivo effects were associated with augmented IL-10 and decreased IFNγ mRNA expression in lymphoid organs. Collectively these data indicate that contemplated compounds can functionally induce a Th2 cytokine bias in vitro and in vivo.

Preparation of Human T-cells and Activation in vitro

Peripheral blood mononuclear cells were isolated from healthy donors or rheumatoid arthritis patients by density gradient centrifugation followed by T cell enrichment using Lymphokwik (One Lambda, Canoga Park Calif.). Contaminating monocytes were removed by adherence to plastic. Purified T cells were >99% CD2+, <1% HLA-DR+ and <5% CD25+ and were maintained in RPMI-AP5 (RPMI-1640 medium containing 20 mM HEPES buffer, pH 7.4, 5% autologous plasma, 1% L-glutamine, 1% penicillin/streptomycin and 0.05% 2-mercaptoethanol).

For determination of cytokine protein levels, T-cells ($1 \times 10^6$ cells in a volume of 1 ml) were activated by the addition of 10 ng PMA plus 0.5 µg ionomycin (both from Calbiochem, La Jolla, Calif.) and incubated in 24 well plates in the presence of 0 to 20 µM nucleoside for up to 48 h at 37° C. and 5% $CO_2$ in a humidified incubator. Following activation, supernatants were analysed for cell-derived cytokine production. For proliferation and viability studies, the protocol as above was modified to a 96 well-plate format using $0.2 \times 10^6$ cells in a volume of 0.2 ml and activation with 2 ng PMA and 0.1 µg ionomycin. In separate experiments, $5 \times 10^6$ T cells in 2 ml were activated with 20 ng PMA plus 1 µg ionomycin. Here total RNA was isolated from T cells following 6–24 h incubation and analyzed by RT-PCR to determine mRNA levels of various cytokines and inflammatory mediators. Also in separate experiments, human T cells were purified further (using cell enrichment reagents from Stem Cell Technologies, Vancouver, BC) to give pure populations of CD4+ (<1% CD8+ using RosetteSep human CD4+ T cell isolation reagent), and CD8+ (<1% CD4+ using RosetteSep human CD4+ T cell isolation reagent) T cell subsets, after which $1 \times 10^6$ cells per ml were activated with PMA and ionomycin, as in the total T cell experiments.

Extracellular Cytokine Analyses

Human cytokine levels were determined in cell supernatants, following appropriate dilution, using ELISA kits specific for IL-2, IFNg, TNFa, IL-4 and IL-5 (Biosource International, Camarillo, Calif.). Murine cytokine levels were determined using ELISA kits specific for murine IFNg and IL-4 (R and D Systems, Minneapolis, Minn.). All ELISA results were expressed as pg/ml. Some data are shown as percentage of activated control, calculated as the ratio of activated T cell cytokine level in the presence of test nucleoside over the cytokine level of untreated activated T cells×100%. Zero effect on cytokine levels by test nucleosides would give a percentage of activated control value of 100%. Alternatively data were shown as percentage change from activated control ([(test pg/ml—activated control pg/ml)/activated control pg/ml]×100%). Zero effect on cytokine levels by test nucleosides would be 0%.

ELISA Spot Assay

ELISA spot plates (Whatman Polyfiltronics, Rockland, Mass.) were coated with the capture antibody in sterile PBS overnight. Mouse monoclonal antibody (mAb) anti-human interferon-g (IFNg, clone MD1, Biosource) was used at 4 mg/ml for IFNg. Anti-IL-2 capture antibody (4 µg/ml, clone 5334.21, R & D Systems) was used for IL-2, anti-IL-4 capture antibody (clone 8D4-8, Pharmingen, San Diego, Calif.) was used at 5 µg/ml for IL-4, and anti-IL-5 capture antibody (5 µg/ml, clone TRFK-5, Pharmingen) was used for IL-5. After washing 2 times with sterile PBS, the plates were blocked for 1.5 h with sterile PBS containing 1% BSA and washed 3 times with sterile PBS afterwards. $0.2 \times 10^6$ PBMC in 200 ml of RPMI medium (containing 1% pen-strep, 1% glutamine and 10% FCS) were placed in each well with 4 µg/ml PHA with or without the nucleoside (10 µM), and cultured for 24 h (IL-2) or 48 h (IL-4, IL-5, IFNγ) at 37° C. in 5% $CO_2$. After washing, biotinylated anti-lymphokine detection antibodies were added overnight, anti-human IFNγ(4 μg/ml, Biosource), anti-IL-2 (3 μg/ml, R and D Systems), anti-IL-4 (2 μg/ml, Pharmingen), and anti-IL-5 (2 μg/ml, Pharmingen). To assess binding of biotinylated antibodies streptavidin-horseradish peroxidase (1:2000 in PBS 0.025% Tween for 1.5 h at room temperature, Vector, Burlingame, Calif.) was used. The plates were developed using 400 μl AEC (Sigma, St. Louis, Mo., 10 mg dissolved in 1 ml dimethyl formamide) mixed in 12 ml 0.1 M sodium acetate buffer, pH 5.0, plus 6 ml $H_2O_2$. The resulting spots were counted on a computer assisted ELISA spot image analyzer (ImmunoSpotTM Image Analyzer, Cellular Technology, Ltd., Cleveland, Ohio.), which is designed to detect ELISA spots using predetermined criteria.

Proliferation and Viability Assay

T cell proliferative responses were assessed by measuring [3H]-thymidine (1 μCi, ICN, Irvine, Calif.) incorporation for the last 16 h of each assay. Cells were harvested onto filters and DNA synthesis was measured following scintillation counting on a Wallac Betaplate counter (Perkin-Elmer/Wallac, Gaithersburg, Md.). Viability was assessed by propidium iodide (5 μg/ml) exclusion in untreated and nucleoside-treated human T cells stained with FITC-CD3 (Becton Dickinson, San Jose, Calif.). The viability of CD3+ cells following addition of propidium iodide (Roche Molecular Biochemicals, Indianapolis, Ind.) was confirmed by flow cytometry (FACScan, Becton Dickinson).

Contact Hypersensitivity (CHS)

Reactivity to the contact allergen, DNFB, was determined, in BALB/c mice, as previously described (Ishii, N., K. Takahashi, H. Nakajima, S. Tanaka, P. W. Askenase. 1994. DNFB contact sensitivity (CS) in BALB/c and C3H/He mice. *J. Invest. Dermatol.* 102:321). Briefly, mice were sensitized by application of 20 μl of 0.3% DNFB in acetone: olive oil, 4:1 onto the shaved abdomens of naive mice. For optimal elicitation of CHS, the mice were challenged on both sides of each ear with 20 μl of 0.12% DNFB, five days after sensitization. Unsensitized mice were also challenged and used as controls in each experiment. After 24 h, ear thickness measurements were taken and response to DNFB was assessed by subtracting post-challenge from pre-challenge values. Where indicated, 7-β-D-ribofuranosyl-4-oxopyrrolo-[2,3-d]pyrimidine-5-carboxamidine, at a dose of 6.2 μg in 50 μl PBS (0.3 mg/kg) or 12.4 μg in 100 μl PBS (0.6 mg/kg), was administered by i.p. injection at the time of challenge with DNFB. These doses of 7-β-D-ribofuranosyl-4-oxopyrrolo[2,3-d]pyrimidine-5-carboxamidine gave maximal effect in preliminary optimization studies. Following final ear thickness measurements, mice were sacrificed by cervical dislocation and axillary/lateral axillary lymph nodes were removed. Following isolation of total cellular RNA from isolated lymph node cells, RT-PCR and Southern Blot analyses were performed to monitor for mouse IFNg, IL-2, and IL-10 mRNA levels.

Staphylococcal Enterotoxin B Treatment in vivo

SEB was injected i.p. at a dose of 50 μg per mouse at day 0 into three groups of 4 mice. One group was injected with 6.2 μg 7-β-D-ribofuranosyl-4-oxopyrrolo[2,3-d]pyrimidine-5-carboxamidine (0.3 mg/kg) and one group with 12.4 μg 7-β-D-ribofuranosyl-4-oxopyrrolo-[2,3-d]pyrimidine-5-carboxamidine (0.6 mg/kg) both in 50 μl PBS i.p., 1 h prior to SEB injection. The 0.6 mg/kg dose of 7-β-D-ribofuranosyl-4-oxopyrrolo[2,3-d]pyrimidine-5-carboxamidine gave maximal effect in preliminary optimization studies. 24 h later all mice were anesthetized with an appropriate dose of the inhalation anesthetic, Penthrane (Abbott Labs, N. Chicago, Ill.) and exanguinated by cardiac puncture to obtain whole blood and spleens were removed. Splenocyte suspensions were prepared from individual spleens following removal of contaminating red cells with ACK lysing buffer (0.15M $NH_4Cl$, 1 mM $KHCO_3$ and 0.1 mM $Na_2EDTA$ adjusted to pH 7.2–7.4 and filtered). Following isolation of total cellular RNA from isolated splenocytes, RT-PCR and Southern Blot analyses were performed to monitor for mouse IFNγ, IL-2, and IL-10 and iNOS mRNA levels. Serum was obtained from clotted blood and used for determinations of nitric oxide production. Nitric oxide production was evaluated by measuring its stable end products, nitrite and nitrate. Total nitrite/nitrate levels were determined following reduction of nitrate to nitrite through a nitrate reductase enzyme reaction followed by a colorometric assay (Sigma) based on the reduction of total nitrite by Griess reagent to a purple azo-compound.

Analysis of Cytokine mRNA

Total cellular RNA was extracted using Trizol reagent (Life Technologies, Gaithersburg, Md.). The cDNA synthesis reaction was performed using oligo (dT)12-18 primer and Superscript II (Life Technologies) reverse transcriptase. The PCR reaction (GeneAmp PCR kit, Perkin-Elmer, Foster City, Calif.) consisted of a 50 μl mixture containing cDNA, dNTPs (each at 200 μM), 0.5 μM of each primer pair and 1.25 unit of Taq polymerase. The primers for human IL-2, IL-10, IL-4, IL-6, IL-1b, IFNg, c-myc, IL-2R, CD40L (Stratagene, La Jolla, Calif.), iNOS (Clontech, Palo Alto, Calif.) and pHE7 ribosomal gene were used. Typical amplification conditions included a 5-minute denaturation at 94° C. and a 5 minute annealing at 60° C. followed by 35 cycles of 1.5 min at 72° C., 45 sec at 94° C. and 45 sec at 60° C., with a final extension time of 10 min at 72° C. The primers for mouse IL-2, IFNγ, and β-actin were obtained from Stratagene and mouse IL-10 from Clontech. Amplification conditions for the Stratagene mouse cytokine primers were a 5 min denaturation at 94° C. and a 5 min annealing at 60° C. followed by 35 cycles of 1.5 min at 72° C., 45 sec at 94° C. and 45 sec at 60° C., with a final extension time of 10 min at 72° C. For IL-10, the PCR conditions were a 5-minute denaturation at 94° C. followed by 35 cycles of 45 sec at 94° C., 45 sec at 60° C. and 2 min at 72° C., with a final extension time of 7 min at 72° C.

For each gene product, the optimum cDNA dilution was determined experimentally and was defined as the cDNA dilution that would achieve a detectable concentration that was well below saturating conditions. PCR products were separated on 2% agarose containing ethidium bromide and immobilized to Hybond N+ membrane (Amersham Pharmacia, Piscataway, N.J.) overnight using 0.4 M NaOH and 0.2M NaCl. Blots were hybridized with 32P-γATP labeled oligonucleotide probes generated from the original primers (Stratagene) or from specific probes designed to be complimentary to a central region within individual PCR products (human iNOS, mouse IL-10 and human pHE7). Equivalent loading was assessed following hybridization with a probe generated from pHE7 sense primer. Washed blots were then analyzed using a Phosphorimager (Biorad, Richmond, Calif.). Relative changes in cytokine or other test mRNA were presented as densitometric readings and normalized for any variations in input RNA by determining the densitometric ratio of mRNA of interest relative to mRNA of the housekeeping gene, pHE7.

Generation of Th1 and Th2 T cells

Eight to ten BALB/c or C57BL/6 mice were sacrificed by cervical dislocation, axillary/lateral axillary and popliteal lymph nodes were removed, lymph node cell suspensions were prepared from each animal and pooled. Murine CD4+ T cells were isolated from pooled lymph node preparations of each mouse strain using StemSep murine T cell enrichment reagent (Stem Cell Technologies). The generation of Th1 and Th2 cells was performed using a protocol similar to that described previously (Austrup, F., D. Vestweber, E. Borges, M. Lohning, R. Brauer, U. Herz, H. Renz, R. Hallmann, A. Scheffold, A. Radbruch, A. Hamann. 1997. P- and E-selectin mediate recruitment of T-helper-1 but not T-helper-2 cells into inflamed tissues. Nature. 385:81). Briefly, cells were activated on 24 well tissue culture plates coated with an optimal amount (1 mg per well) of anti-CD3 mAb (clone 145-2C11, Pharmingen) in the presence of the indicated recombinant murine cytokines and cytokine Abs (all from Pharmingen) (IL-2 alone, 50 U/ml; Th1: IL-2, 50 U/ml; IL-12, 1000 U/ml; IFNg with and without 10 mM ICN 10776 and Th2: IL-2, 50 U/ml; IL-4, 10 ng/ml; anti-IFNg (clone XMG1.2)10 mg/ml) and cultured for 4 days. Cells were transferred to fresh plates without medium change and incubated for a further 48 h then washed three times and fresh medium added, incubated overnight then restimulated for 5 h with PMA (long) and ionomycin (0.5 mg). Cell free supernatants were then taken for ELISA determination of murine IL-4 and IFNg levels. Cells that were not restimulated were negative for IL-4 and IFNγ, indicating that the cytokine added during culture was not carried over.

Statistical Analysis

Trend analysis was performed using one-way or two-way ANOVA analysis. Statistical significance, where relevant, was assessed using the Student-Newman-Keuls multiple comparison method.

Results

Figure 13A:
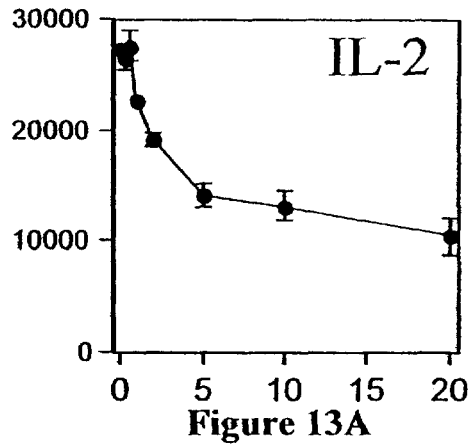
FIGS. 13A–13F are graphs depicting dose effect of contemplated compounds on cytokine and proliferative responses in activated human T-cells.
Figure 13B:
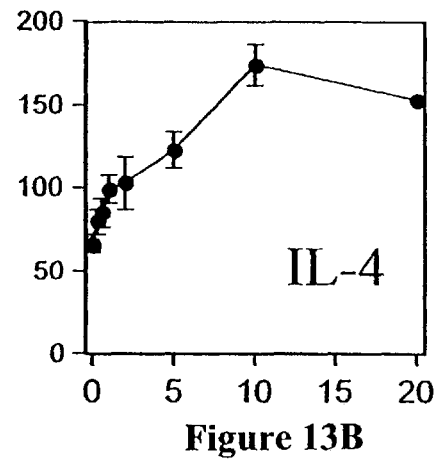
Figure 13C:
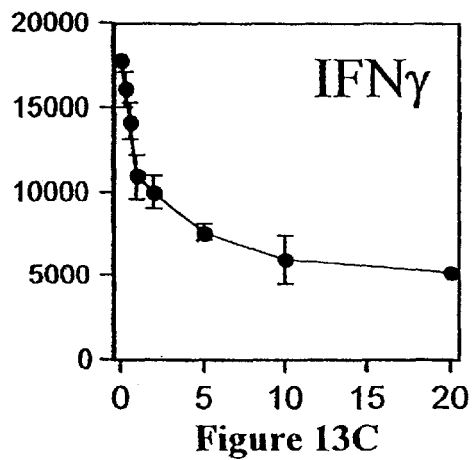
Figure 13D:
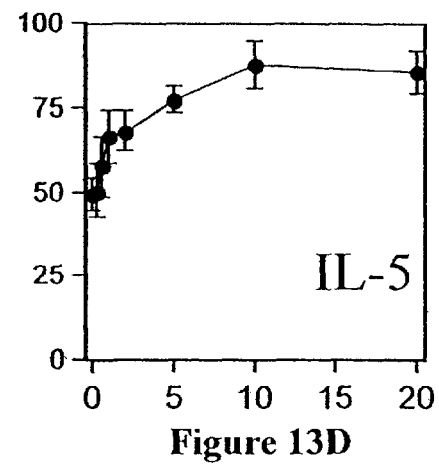
Figure 13E:
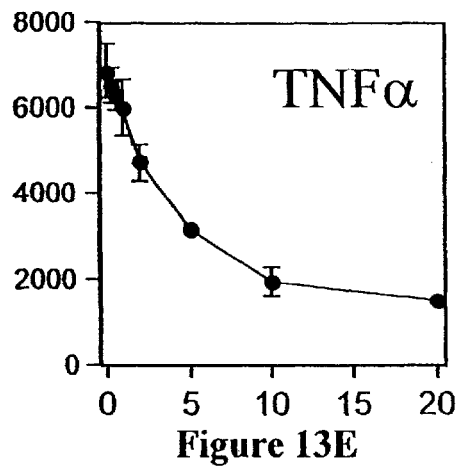
Figure 13F:
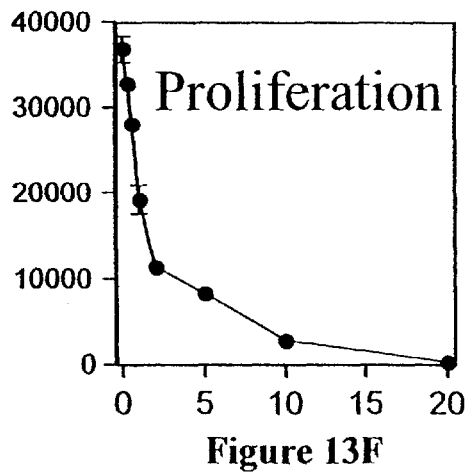

The Dose Effect of ICN 10776 on Cytokine and Proliferative Responses by Activated Human T Cells We examined the Type 1 and Type 2 cytokine profile, as well as the influence on T cell proliferative responses, induced by a 48 h incubation of 7-β-D-ribofuranosyl-4-oxopyrrolo-[2,3-d]pyrimidine-5-carboxamidine (ICN 10776) with activated peripheral human T cells. In the dose range 0.2 to 20 $\mu$M, ICN 10776 enhanced PMA-ionomycin (PMA-ION)-induced levels of the Type 2 cytokines, IL-4 and IL-5, in a dose-dependent manner with a peak enhancement at 10 $\mu$M of 166% and 77% respectively (FIGS. 13B, 13D). The data shown are from a representative of five donors. In addition, in the same dose range and also in a dose-dependent manner, ICN 10776 dramatically suppressed PMA-ION-induced levels of the Type 1 cytokines, IL-2, IFNγ and TNFα with a peak suppression of 62%, 72% and 78% respectively at 20 $\mu$M (FIGS. 13A, 13C, 13E), as well as substantially inhibiting T cell proliferation with a peak inhibition of 99% at 20 $\mu$M (FIG. 13F). A second proliferation assay was also performed using a calorimetric assay (MTT cell proliferation kit I, Roche Molecular Biochemicals) based on the conversion of the tetrazolium salt, MTT by mitochondrial dehydrogenases to a formazan dye (detectable at 540 nm). Using this assay ICN 10776 also dramatically inhibited T cell proliferation (data not shown) demonstrating that the effect by ICN 10776 was not due to interference of thymidine uptake as has been demonstrated for other nucleoside analogues. Similar effects on cytokine modulation were seen in T cells and PBMCs stimulated with PHA (data not shown).

Figure 14:
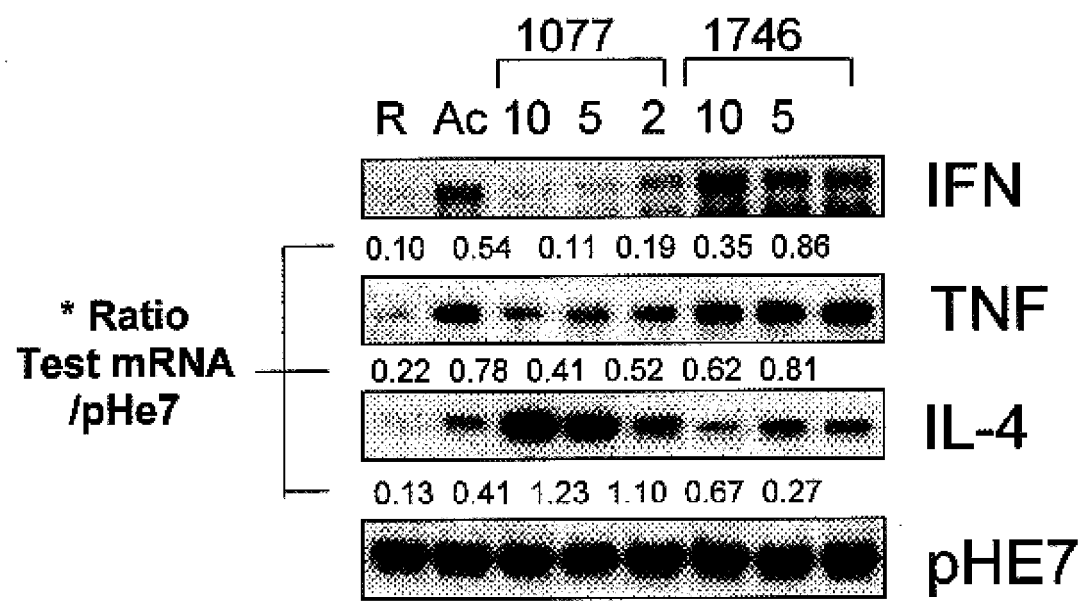
FIG. 14 is an autoradiograph showing various RNA expressions in cells in response to treatment with contemplated compounds.

In a second set of experiments, T cells were activated with PMA-ION alone or in the presence of 2, 5 or 10 $\mu$M ICN 10776 or its L-enantiomer, ICN 17465, for 6 h or 24 h prior to RNA isolation and RT-PCR analyses to determine levels of Type 1 and Type 2 cytokine mRNA. We observed that with increasing doses of ICN 10776 there was an increase in IL-4 mRNA and a concomitant decrease in IFNγ and TNFα mRNA (FIG. 14, showing data from a representative of three donors). Interestingly, no similar modulation of the activated levels of these cytokines were observed with the L-enantiomer of ICN 10776, ICN 17465, demonstrating an absolute requirement for a D-ribose sugar moiety for bioactivity (FIG. 14).

Figure 15A:
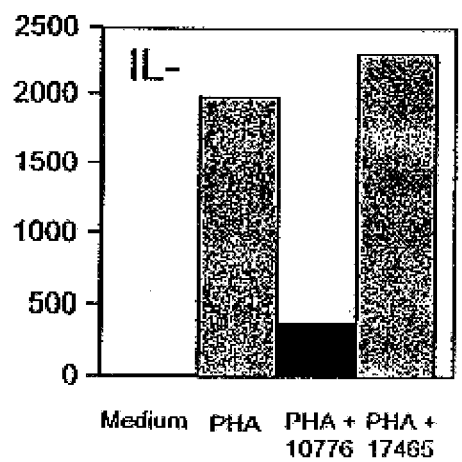
FIGS. 15A–15D are graphs depicting the number of specific cytokine producing cells in response to treatment with contemplated compounds.
Figure 15B:
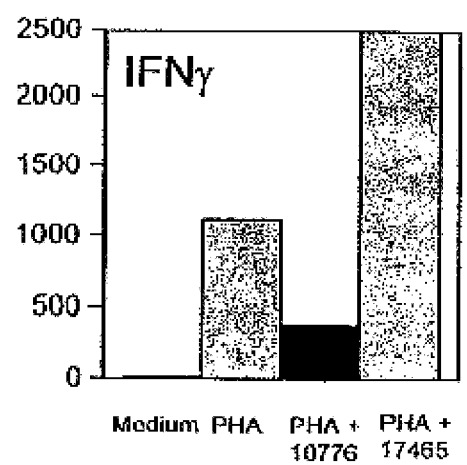
Figure 15C:
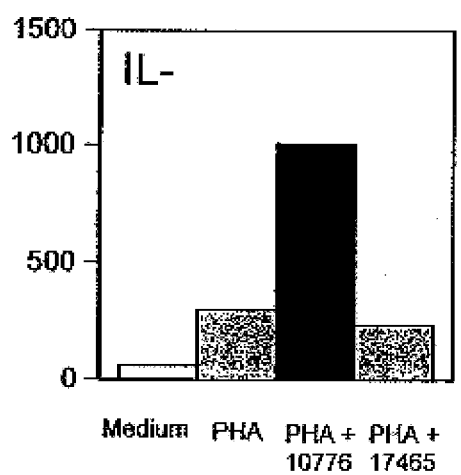
Figure 15D:
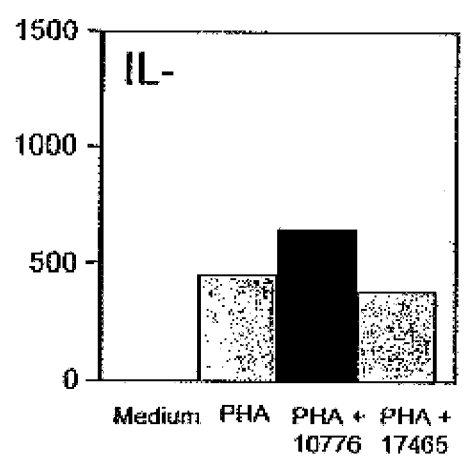

In a third set of experiments, PBMCs were activated with PHA alone or in the presence of 10 $\mu$M ICN 10776 or its L-enantiomer, ICN 17465, for 24–48 h on specific cytokine antibody bound ELISA spot plates. The number of specific cytokine producing cells were then determined as described previously. A dramatic fall in the number of IL-2 and IFNγ-producing cells were observed in the presence of ICN 10776 but not the L-enantiomer, ICN 17465 (FIGS. 15A–B). In contrast ICN 10776, but not the L-enantiomer, ICN 17465 induced a substantial increase in the number of both IL-4 and IL-5 producing cells (FIGS. 15C–D).

Altogether these data show that ICN 10776 reduces both the production of Type 1 cytokines and T cell proliferation while elevating levels of Type 2 cytokines in a dose-related manner. The effects of ICN 10776 on cytokine responses were observed at the protein and mRNA levels and affected the number of specific cytokine producing cells. Moreover, the induction of a Type 2 cytokine bias required D-ribosylation as the L-enantiomer of this nucleoside did not show similar bioactivity.

Figure 16A:
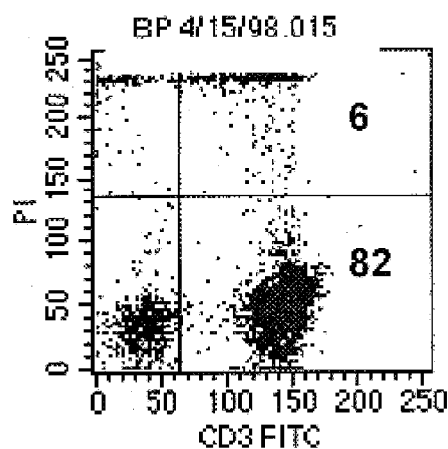
FIGS. 16A–16F are graphs depicting temporal effects of contemplated compounds on viability, cytokine responses, and proliferation of activated human T cells.
Figure 16B:
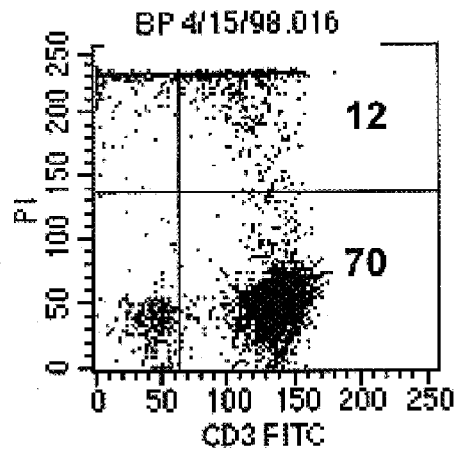
Figure 16C:
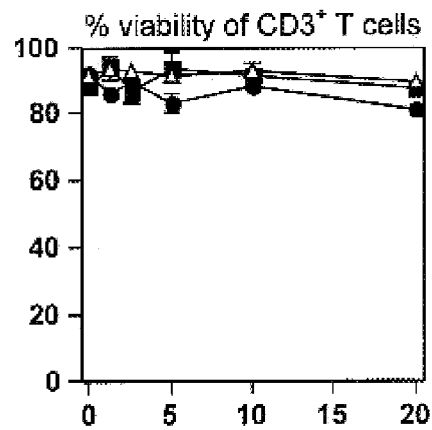
Figure 16D:
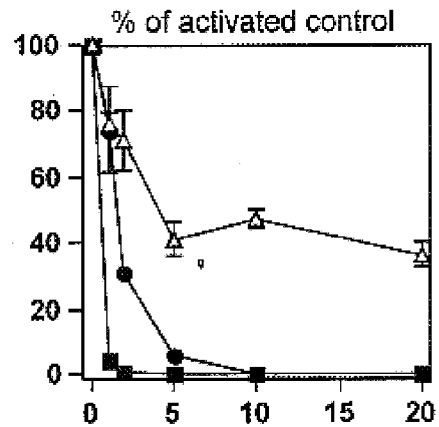
Figure 16E:
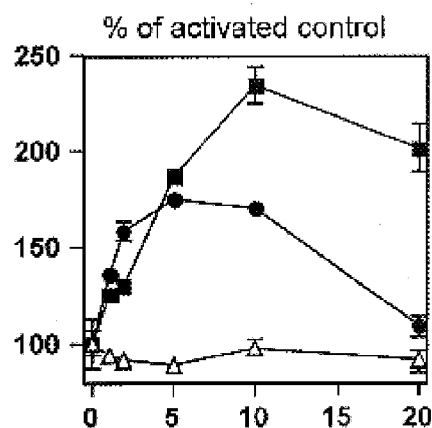
Figure 16F:
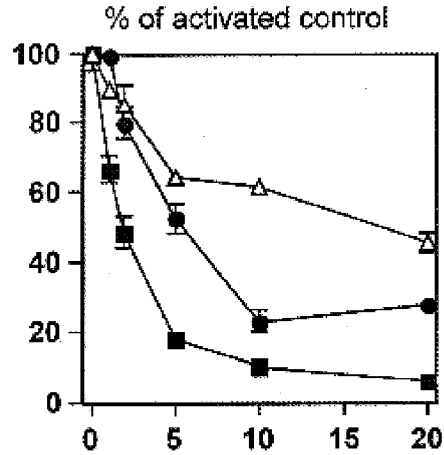

The Temporal Effect of ICN 10776 on Viability, Cytokine Responses and Proliferation of Activated Human T Cells We determined whether the suppression of Type 1 cytokine expression and the inhibition of T cell proliferative responses were merely the product of T cell toxicity by ICN 10776. If toxicity were responsible for these observations then viability of T cells would be influenced by both incubation time and dose of ICN 10776. Using propidium iodide exclusion analyses we observed that viability did decrease in resting CD3$^+$ T cells from 95% to 85% following 48 h incubation with 20 $\mu$M 10776 (FIGS. 16A–B). In PMA-ION activated CD3$^+$ T cells without nucleoside treatment, a temporal decrease in viability was observed from 91±1% at 8 h to 88±2% at 24 h to 83±1% at 48 h however no sign difference to these numbers was found in the presence of nucleoside across the dose range 0.2 to 20 $\mu$M of ICN 10776 (FIG. 16C). These data suggest that the small decrease in viability was induced presumably by activation-induced apoptosis of T cells and not a direct toxic effect by the nucleoside. Moreover, the temporal effect of incubation with ICN 10776 did show a dose-dependent decrease in T cell proliferation (FIG. 16D) and IFNγ secretion (FIG. 16F) but with peak suppression at 48 h. Likewise, the peak dose-dependent increase in IL-4 was also observed at 48 h (FIG. 16E). These data showed that the biologic effects observed following treatment with ICN 10776 were not the result of in vitro toxicity and had a peak effect after 48 h incubation. The decline in effect after 48 h may be related to metabolism of the nucleoside to inactive degradation products via dephosphorylation or deribosylation.

Figure 17A:
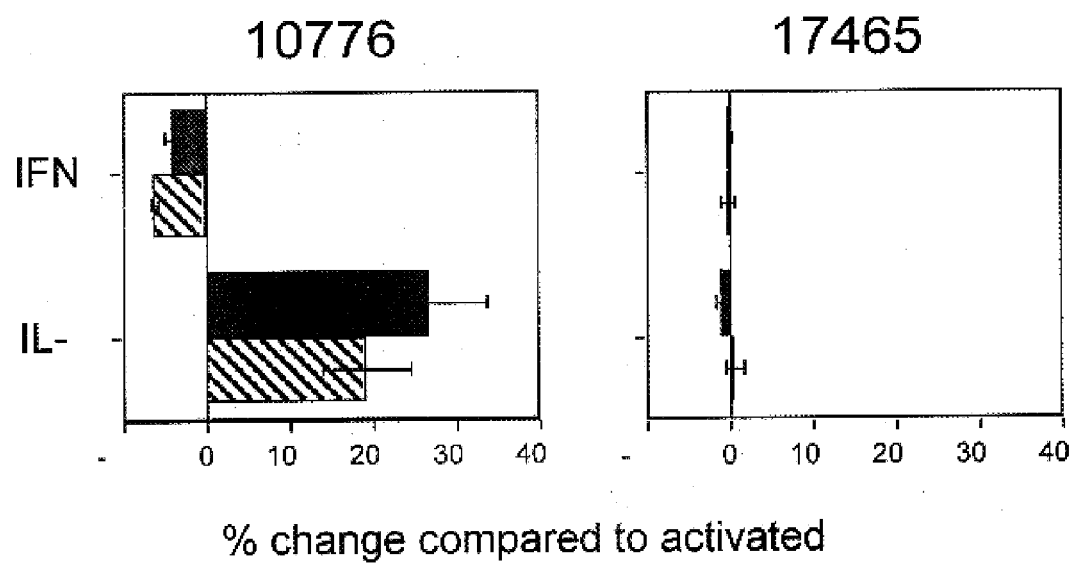
FIGS. 17A and 17B are graphs depicting comparative effects of contemplated compounds on cytokine production in activated peripheral T cells from normal donors and rheumatoid arthritis patients.
Figure 17B:
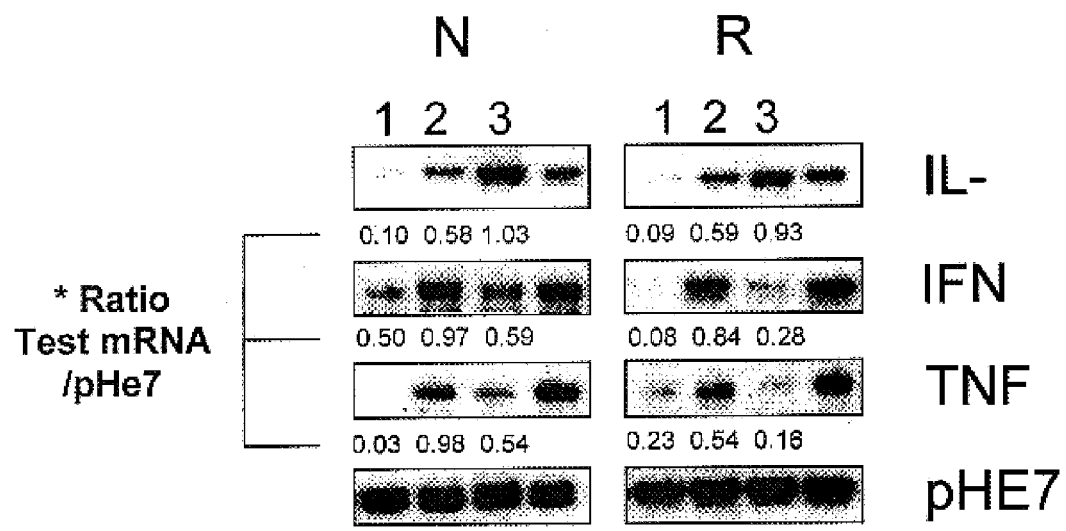

Comparative Effects of ICN 10776 on TNFα, IFNγ and IL-4 Production in Activated Peripheral T Cells from Normal Donors and Rheumatoid Arthritis Patients It has been previously shown that in vitro differentiation of peripheral T cells towards a Type 2 phenotype is impaired in rheumatoid arthritis (RA) patients when compared to normal donors (Berg, D. J., M. W. Leach, R. Kuhn, K. Rajewski, W. Muller, N. J. Davidson, D. Rennick, 1995. Interleukin 10 but not interleukin 4 is a natural suppressant of cutaneous inflammatory responses. *J. Exp. Med.* 182:99). Here we compared the effect of ICN 10776 on the activated cytokine profiles from PMA-ION-activated peripheral T cells of 16 normal donors and 16 RA patients. We observed that the Type 2 cytokine bias induced by 10 μM ICN 10776 occurred in activated peripheral T cells from both normal donors and RA patients, as determined by reduced levels of secreted IFNγ (43% and 63% respectively, p=0.0008 that ICN 10776<than untreated group and ICN 17465 group) and heightened IL-4 production (266% and 192% respectively, p<0.0001 that ICN 10776>than untreated group and ICN 17465 group) (FIG. 17A, left panel). Although cytokine responses were significantly greater in the normal group (p<0.0001), there was no significant difference in the magnitude of Type 2 cytokine bias induced by ICN 10776 in either group (FIG. 17A, left panel). No similar effect on the activated cytokine profile in either group was observed following exposure of peripheral T cells to 10 μM ICN 17465, the L-enantiomer of ICN 10776 (FIG. 17A, right panel). In separate experiments, the activated cytokine mRNA profiles of PMA-ION-stimulated peripheral T cells from both normal donors and RA patients in the presence and absence of 10 μM ICN 10776 and ICN 17465 were determined. As seen with the secreted cytokine protein data above, ICN 10776, but not ICN 17465, elevated IL-4 mRNA levels and suppressed IFNγ and TNFα in peripheral T cells from both subject groups (FIG. 17B). Therefore the induction of a Type 2 cytokine bias both at protein and mRNA levels by ICN 10776 represents a general phenomenon in peripheral blood T cells and appears to be not impaired in peripheral T cells from RA patients.

Figure 18:
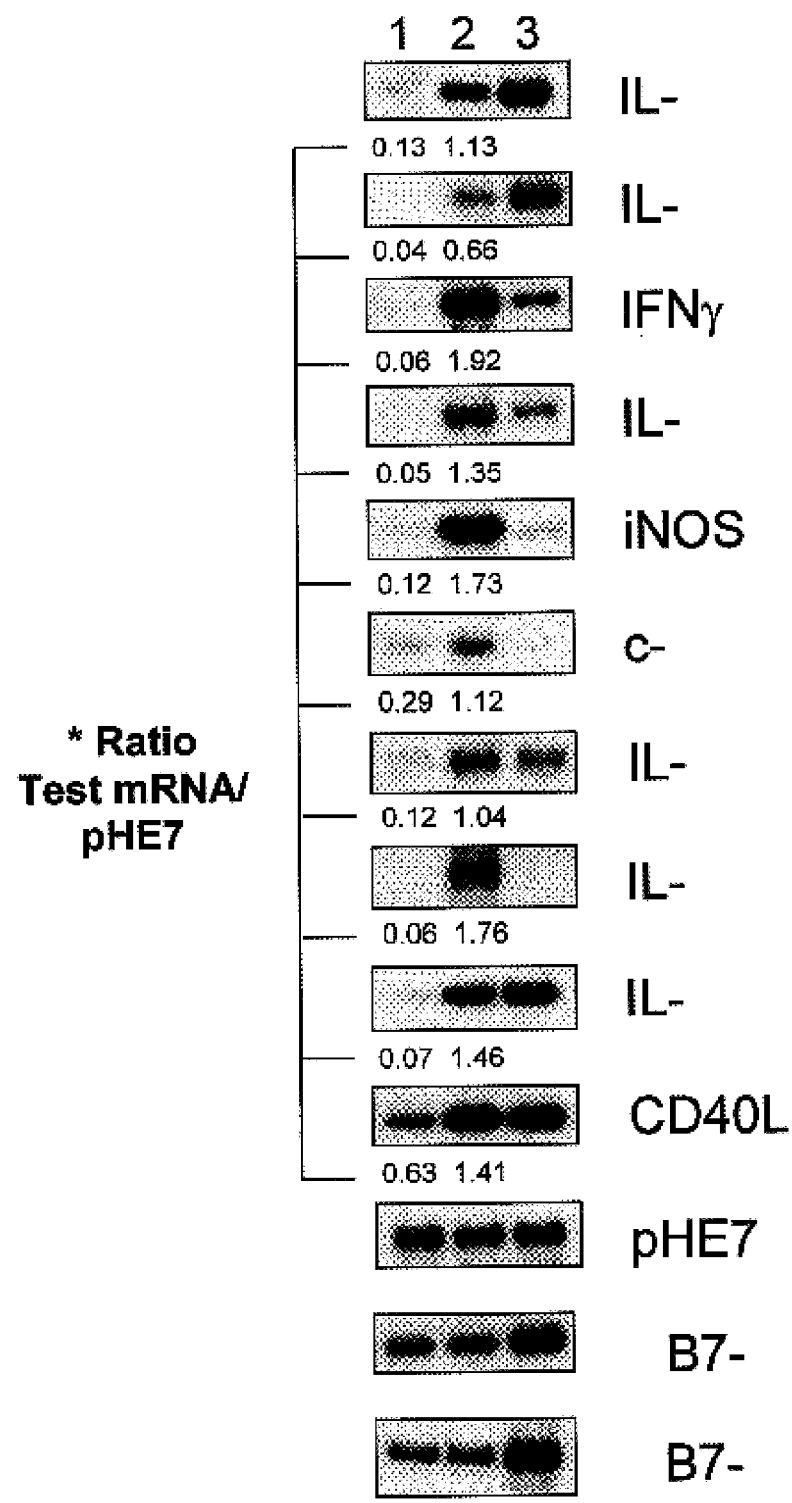
FIG. 18 is an autoradiograph showing various RNA expressions in cells in response to treatment with contemplated compounds.

The Influence of ICN 10776-mediated Cytokine Responses on Pro- and Anti-inflammatory Mediators As a Type 1 cytokine bias generally induces pro-inflammatory responses whereas a Type 2 cytokine bias usually leads to anti-inflammatory responses, we determined the mRNA levels of Type 1 and Type 2 cytokines in activated human T cells and compared the expression of these with mRNA levels of certain critical anti-inflammatory or pro-inflammatory mediators in cells from the same donor. We observed that ICN 10776, in addition to its influence on Type 1 (suppression of IFNγ, TNFα and IL-2) and Type 2 cytokines (enhancement of IL-4) also induced enhancement of IL-10, an anti-inflammatory cytokine, and suppressed levels of two pro-inflammatory cytokines, IL-6 and IL-1β. In addition, concomitant reduction in the expression of inducible nitric oxide synthase (iNOS), an enzyme responsible for the generation of the pro-inflammatory mediator, nitric oxide was also observed (FIG. 18). Furthermore, an anti-proliferative effect by ICN 10776 was evident due to the suppression of the proto-oncogene, c-myc, a gene which is upregulated in proliferating lymphocytes (FIG. 18). These data show that the heightened Type 2 cytokine response and diminished Type 1 cytokine response elicited by ICN 10776 treatment results in an increased anti-inflammatory environment as well as a marked anti-proliferative effect in peripheral T cells.

Figure 19:
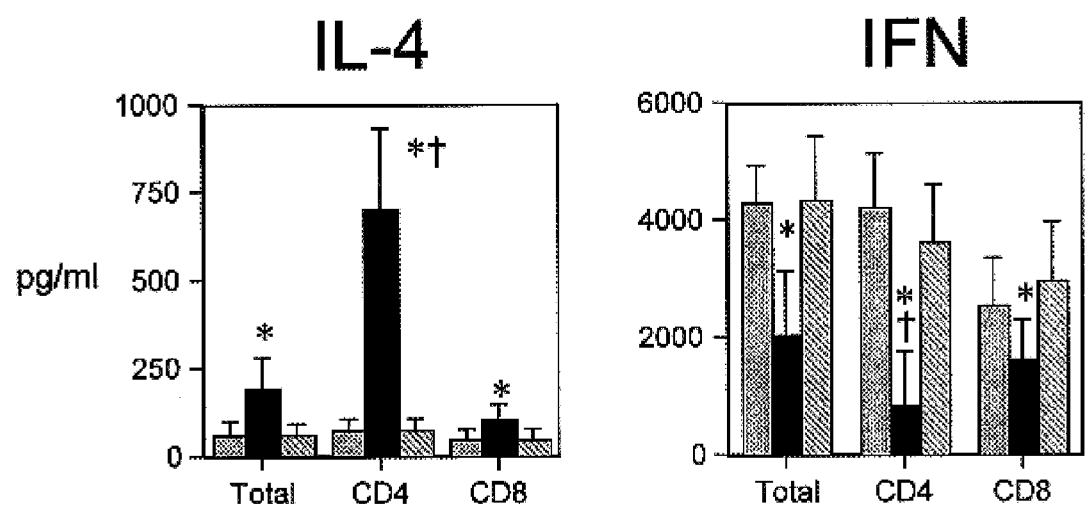
FIG. 19 is a graph depicting the influence of contemplated compounds on activated cytokine responses in $CD4^+$ and $CD8^+$ T cell subsets.

The Influence of ICN 10776 on Activated Cytokine Responses in $CD4^+$ and $CD8^+$ T Cell Subsets The T helper ($CD4^+$) and cytotoxic ($CD8^+$) T cell subsets both play important roles in the immune response to antigens, whether foreign or self. Both subsets can be differentiated to produce either Type 1 or Type 2 cytokines. As $CD4^+$ and $CD8^+$ T cells play distinct roles both in the pathogenesis of autoimmunity and protective response to pathogens, it was important to distinguish any differential effects of the induction of a Type 2 cytokine bias by ICN 10776 in these two T cells subsets. We thus compared the ICN 10776-mediated activated cytokine response in isolated $CD4^+$ and $CD8^+$ T cells and total T cells from the same donor. Secreted IL-4 levels were significantly enhanced in all T cell groups following 48 h stimulation with PMA-ION in the presence of ICN 10776 (black bars), but not in the presence of 17465 (hatched bars), when compared to untreated activated controls (dotted bars)(p<0.0001 that ICN 10776>untreated and ICN 17465) (FIG. 19). In addition, IFNγ levels were significantly reduced in all three T cell groups compared to activated control or ICN 17465-treated groups (p<0.0001). Surprisingly, the ICN 10776-mediated enhancement of IL-4 was most dramatic in $CD4^+$ T cells (994% increase over activated control compared to 228% and 320% in $CD8^+$ T cells and total T cells respectively, p<0.03). Furthermore, the suppression of IFNγ by ICN 10776, although significant in all three T cell groups, was again far more dramatic in $CD4^+$ T cells (81% decrease over activated control compared to 37% and 52% decrease in both $CD8^+$ T cells and total T cells respectively, p<0.05) (FIG. 19). No similar suppressive effect was observed in all three T cell groups following treatment with ICN 17465. These data show that $CD4^+$ T cells were the most susceptible to cytokine modulation by ICN 10776. It also suggests that $CD8^+$ T cells may be more resistant to the ICN 10776-mediated effects and may actually provide a regulatory signal to $CD4^+$ T cells, which dampens the Type 2 cytokine bias induced by ICN 10776.

The Effect of ICN 10776 on Generation of Murine Th1 Cells

Figure 20:
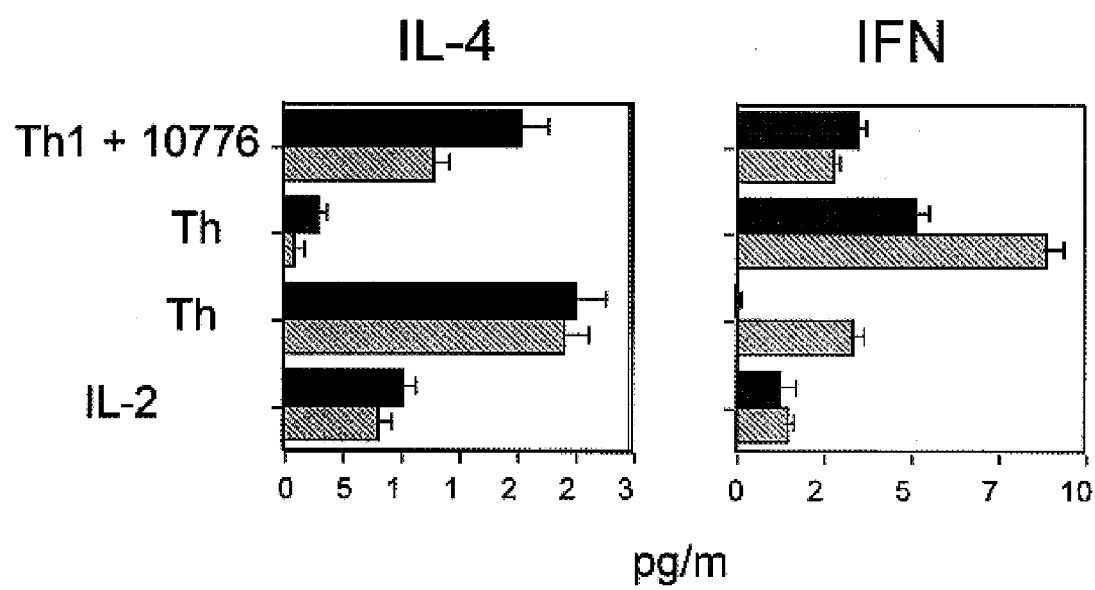
FIG. 20 is a graph depicting the effect of contemplated compounds on murine Th1 cells.

We determined whether ICN 10776 could induce a Type 2 cytokine bias even under conditions, which normally generate Th1 T cells in mouse lymphoid T cells. BALB/c and C57BL/6 lymph node T cells were isolated and Th1 cells were generated following initial incubation in the presence of plate bound anti-CD3 Ab and IL-2, IFNγ and IL-12 as described previously (Austrup, F., D. Vestweber, E. Borges, M. Lohning, R. Brauer, U. Herz, H. Renz, R. Hallmann, A. Scheffold, A. Radbruch, A. Hamann, 1997. P- and E-selectin mediate recruitment of T-helper-1 but not T-helper-2 cells into inflamed tissues. *Nature.* 385:81). These Th1 cells upon restimulation secreted low levels of IL-4 and substantial amounts of IFNγ when compared to anti-CD3 Ab and IL-2 treatment alone (FIG. 20). Co-incubation with ICN 10776 in the first incubation period however induced these murine T cells to produce the elevated levels of IL-4 and low levels of IFNγ similar to those observed in Th2 cells (generated following restimulation in T cells treated with anti-CD3 Ab and IL-2, IL-4 and anti-IFNγ) (FIG. 20). These observations were consistent in both mouse strains. Collectively these data show that ICN 10776 can induce the generation of Th2 cells even in conditions, which are conducive to generating Th1 cells.

Figure 21:
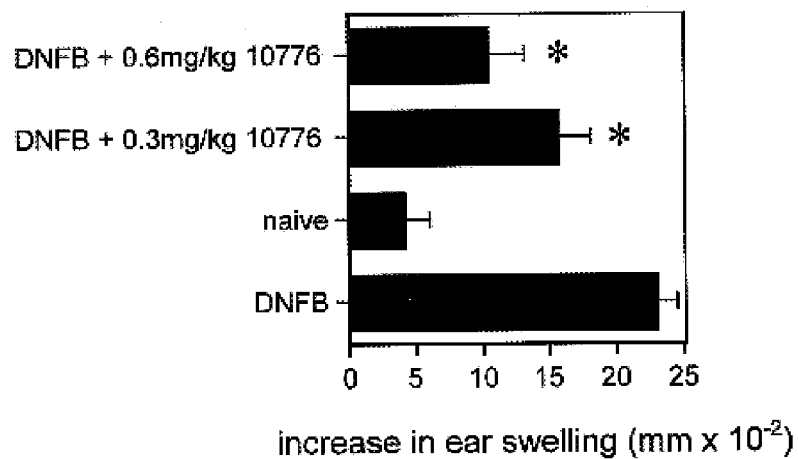
FIG. 21 is a graph depicting the in-vivo effect of contemplated compounds on ear swelling measurements.
Figure 22:
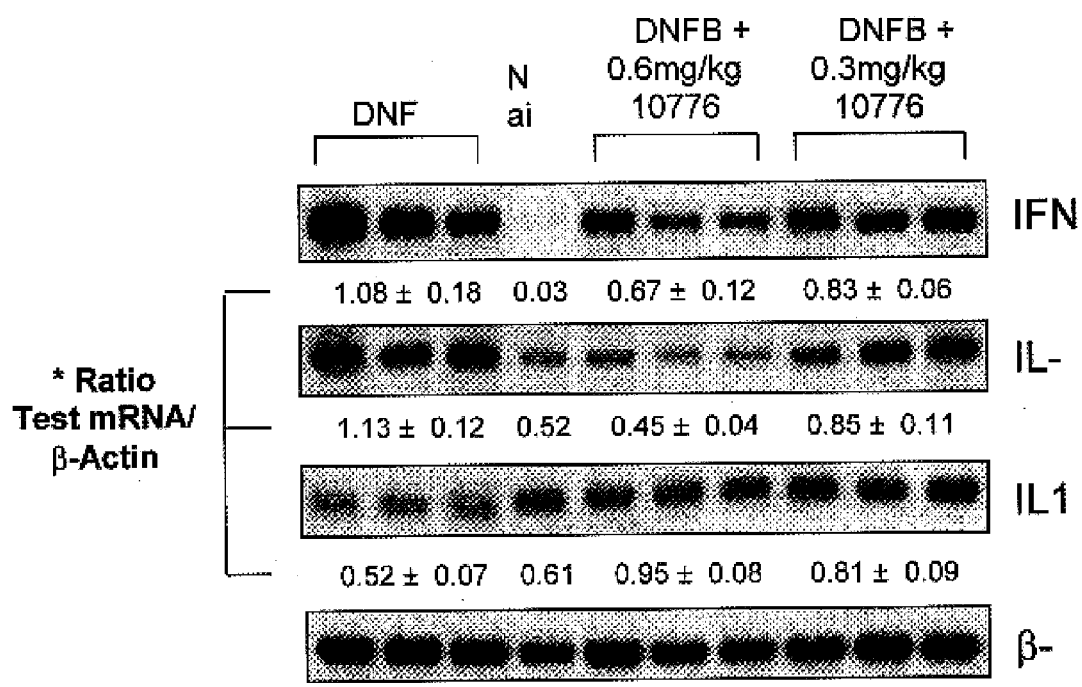
FIG. 22 is an autoradiograph showing various RNA expressions in cells in response to treatment with contemplated compounds.

Impaired contact hypersensitivity responses following ICN 10776 administration is associated with elevated IL-10 expression and reduced IL-2 and IFNγ expression in mouse lymph node cells Contact hypersensitivity (CHS) responses were elicited in DNFB-primed BALB/c mice following ear challenge with 0.2% DNFB as described previously (Ishii, N., K. Takahashi, H. Nakajima, S. Tanaka, P. W. Askenase. 1994. DNFB contact sensitivity (CS) in BALB/c and C3H/He mice. *J. Invest. Dermatol.* 102:321). FIG. 21 shows the ear swelling measurements, following challenge, determined in DNFB-primed and naive mice, and in DNFB-primed mice treated with 0.3 mg/kg and 0.6 mg/kg ICN 10776. In this representative experiment, i.p. injection of ICN 10776, at the time of challenge, greatly impaired CHS responses to DNFB in a dose dependent manner as shown by a mean decrease in ear thickness of 42% with a 0.3 mg/kg dose and 68% with a 0.6 mg/kg dose at 24 h post-challenge (inhibition of CHS was calculated following subtraction of responses in unprimed mice challenged with DNFB (naive)). No substantial changes in post-challenge ear thickness were observed in DNFB-primed mice challenged with acetone:olive oil or in mice primed with acetone:olive oil and challenged with DNFB. In addition, as shown in FIG. 22, mRNA expression of murine IL-10 was greatly enhanced but IL-2 and IFNγ mRNA levels were substantially reduced from lymph node cells in ICN 10776-treated, DNFB-primed mice when compared to DNFB-primed mice alone. Collectively, these data demonstrate that the reduction of in vivo CHS responses in BALB/c mice by ICN 10776 was associated with elevation of IL-10, the principal regulatory cytokine in CHS responses to DNFB, and suppression of IL-2 and IFNγ, both important mediators of CHS responses.

Impaired SEB-induced inflammatory responses as assessed by nitric oxide release following ICN 10776 administration in vivo is associated with elevated IL-10 expression and reduced IFNγ expression in mouse splenocytes.

Figure 23A:
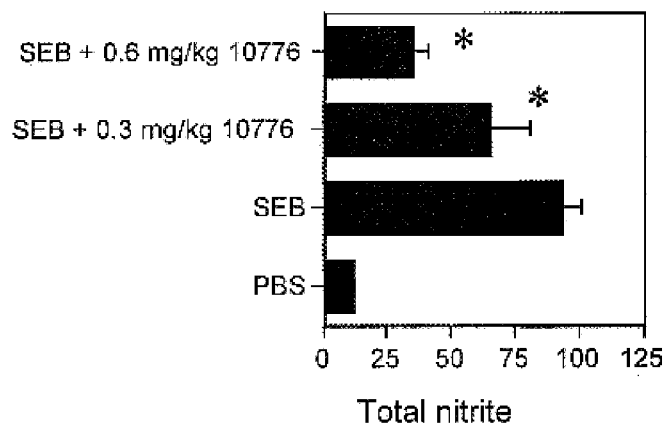
FIGS. 23A and 23B are graphs depicting the in-vivo effect of contemplated compounds on ear swelling measurements and related gene expression.
Figure 23B:
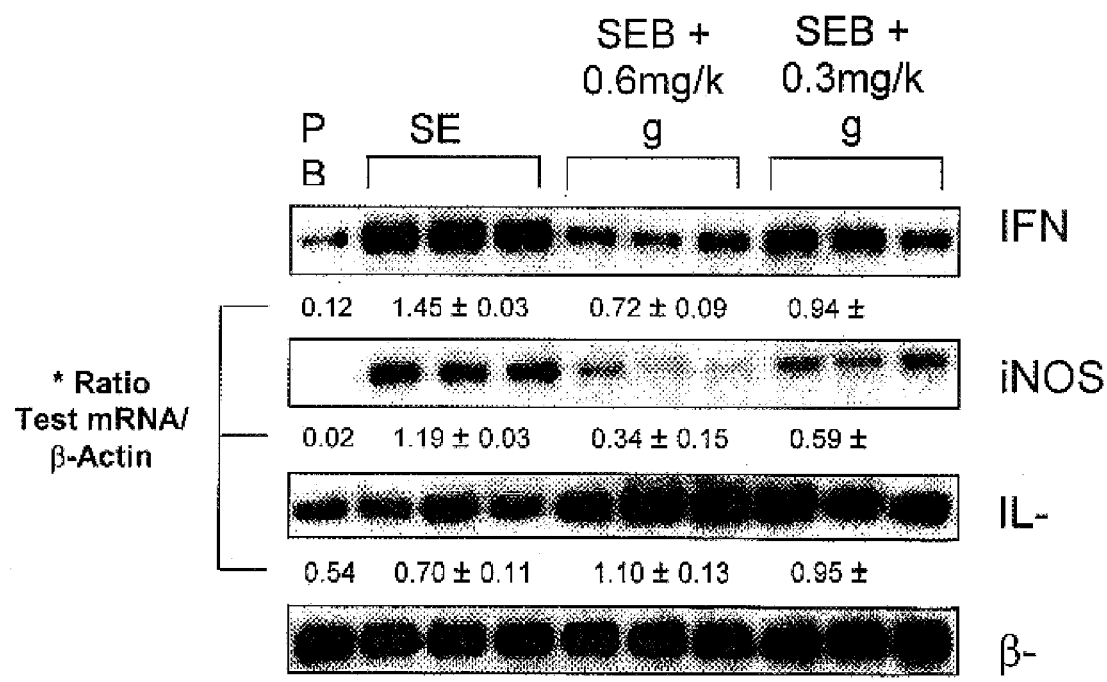

SEB-induced inflammatory responses were elicited in BALB/c mice following ip injection with 50 μg SEB as described previously (Tam, R. C., K. Ramasamy, J. Bard, B. Pai, C. Lim, D. R. Averett. 2000. The ribavirin analog ICN 17261 demonstrates reduced toxicity and antiviral effects with retention of both immunomodulatory activity and reduction of hepatitis-induced serum alanine aminotransferase levels. *Antimicrob. Agents. Chemother.* 44:1276). FIG. 23A shows the total serum nitrite measurements, following SEB challenge, determined in mice treated with 0, 0.3 mg/kg or 0.6 mg/kg ICN 10776. In this representative experiment, i.p. administration of ICN 10776, at the time of challenge, greatly impaired inflammatory responses to SEB in a dose dependent manner as shown by a mean decrease in serum nitrite levels of 54% with a 0.3 mg/kg dose and 78% with a 0.6 mg/kg dose at 24 h post-challenge. In addition, as shown in FIG. 23B, mRNA expression of murine IL-10 was greatly enhanced but IFNγ mRNA levels were substantially reduced from splenocytes in ICN 10776-treated, SEB-challenged mice when compared to SEB-challenged mice alone. Collectively, these data demonstrate that the reduction of in vivo SEB-induced inflammatory responses in BALB/c mice by ICN 10776 was associated with elevation of the anti-inflammatory cytokine, IL-10, a principal regulatory cytokine in SEB-induced inflammatory, and suppression of IFNγ, an important mediator of SEB-induced inflammatory responses.

Figure 24:
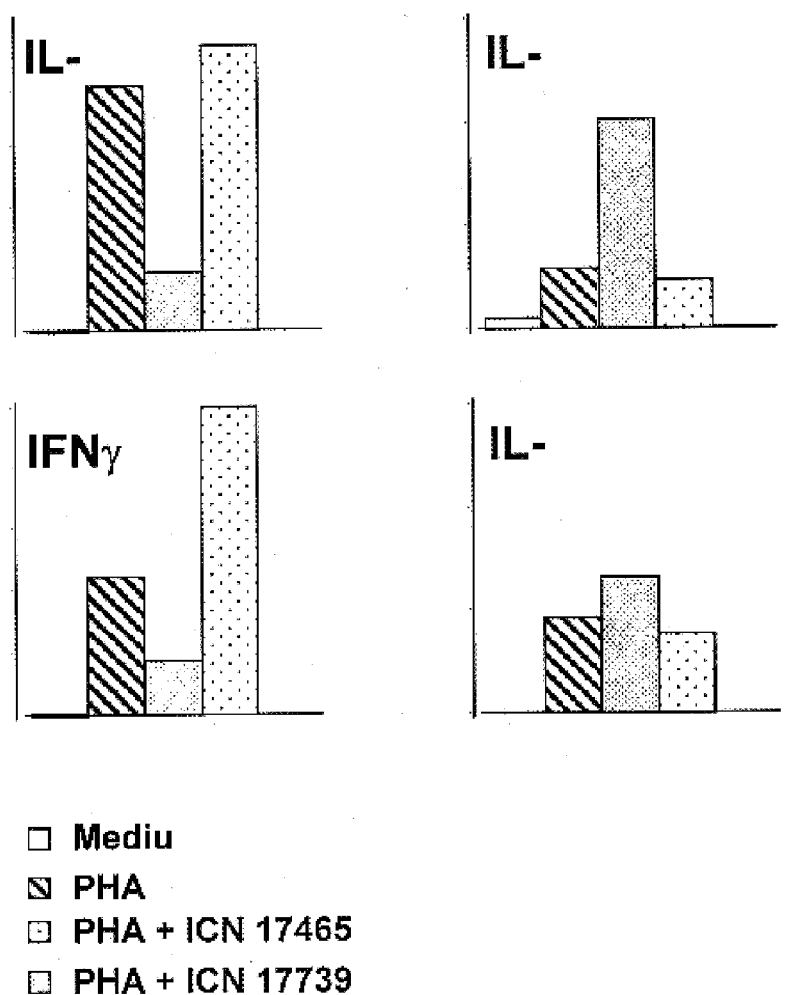
FIG. 24 is a graph depicting reduction of Type 1 and increase of Type 2 cytokines in T-cells treated with contemplated compounds.

Similar data are obtained when ICN 10776 is replaced with its HCl salt (ICN 17739; 7-(β-D-ribofuranosyl)pyrrolo [2,3-d]-4-pyrimidone-5-carboxamidine Hydrochloride). FIG. 24 depicts a significant decrease in Type 1 cytokines in PHA stimulated T-cells versus a significant increase in the production of Type 2 cytokines. Preparation and stimulation of human T-cells was substantially performed as described above. Interestingly, the L-isomer of ICN 10776 (ICN 17465) appears to have an effect uncorrelated to the effect of ICN 17739.

Figure 25:
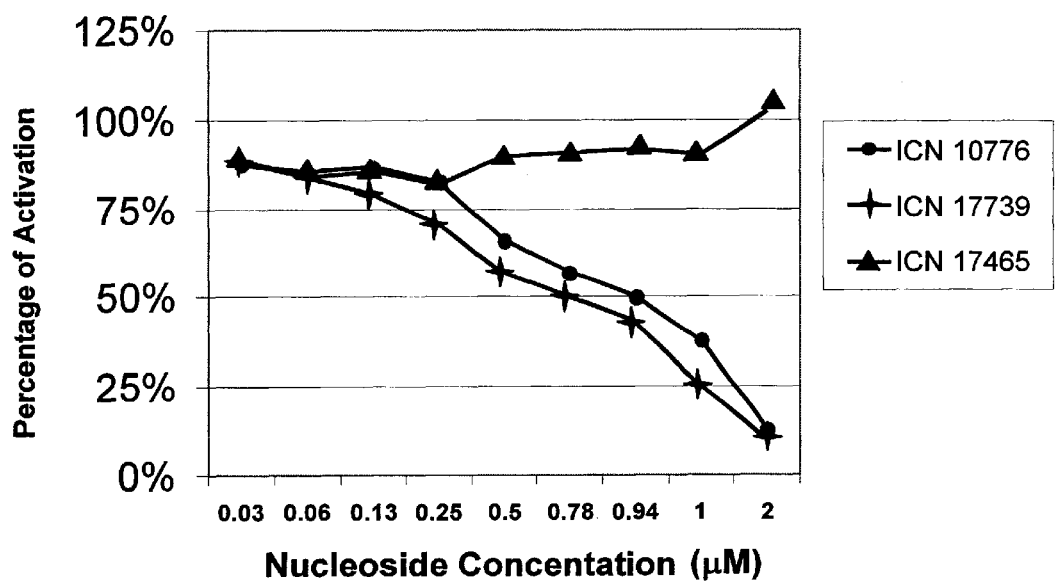
FIG. 25 is a graph depicting inhibition of T-cell proliferation.
Figure 26:
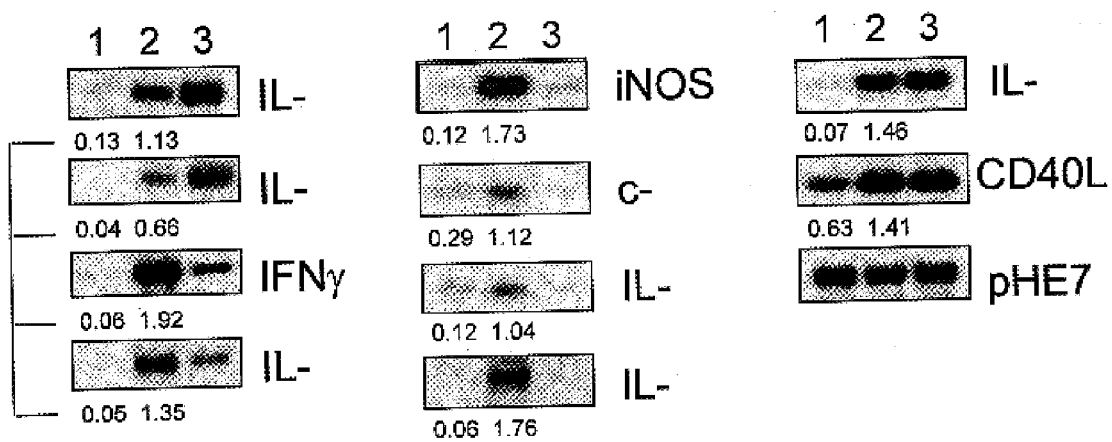
FIG. 26 is an autoradiograph depicting induction of anti-inflammatory and anti-proliferative responses.

Likewise, ICN 17739 has a similar effect on T-cell proliferation in a dose-dependent manner as depicted in FIG. 25. The control ICN 17465 has no apparent inhibitory effect in the shown concentration range under conditions similar to those outlined above. In an experiment corresponding to the experiment depicted in FIG. 18, ICN 17339 showed clearly (FIG. 26) to exhibit induction of anti-inflammatory and anti-proliferative responses.

Figure 27:
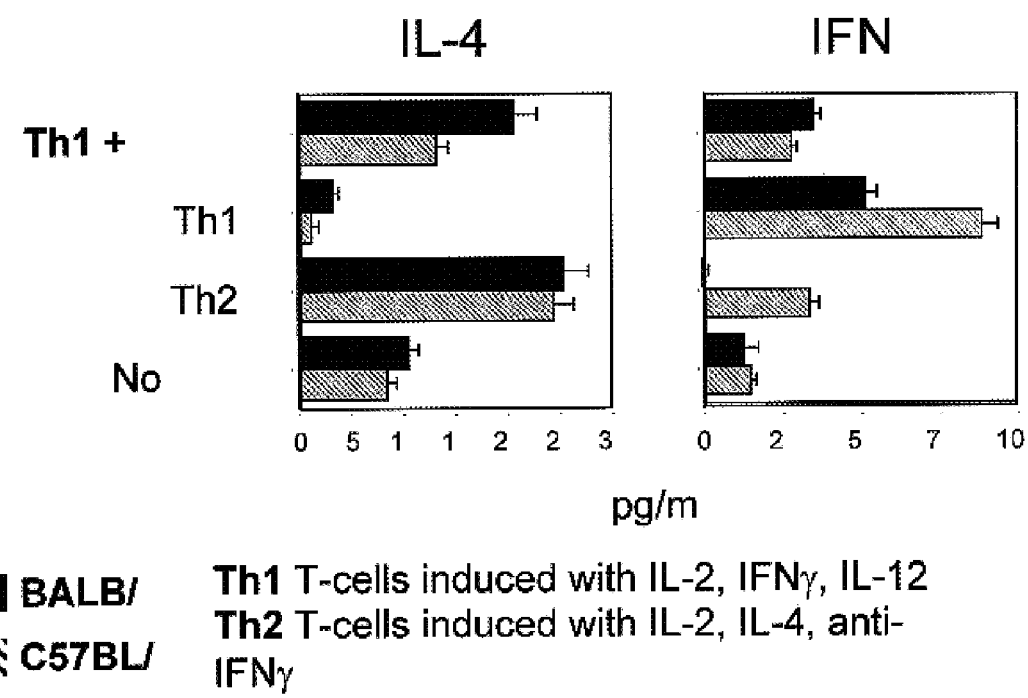
FIG. 27 is a graph depicting override of Th1 response in induced $CD4^+$ cells.

Interestingly, ICN 17739 was able to override a Th1 response in murine CD4$^+$ cells. FIG. 27 depicts the results from 2 independent experiments (first experiment with BALB/c mice, second experiment with C57BL/6) in which Th1 cells were induced with IL-2, IFN-γ, and IL-12. When presented with ICN 17739, such cells significantly increased IL-4 production when compared to incubation without ICN17739. Th2 cells induced with IL-2, IL-4, and anti-IFN-γ showed a strong IL-4 secretion versus moderate increase as compared to induction with IL-2. Similarly, when presented with ICN 17739, induced Th1 cells significantly decreased IFN-γ production when compared to incubation without ICN17739, and Th2 cells induced with IL-2, IL-4, and anti-IFN-γ showed a decreased IFN-γ secretion as compared to induction with IL-2.

Figure 28:
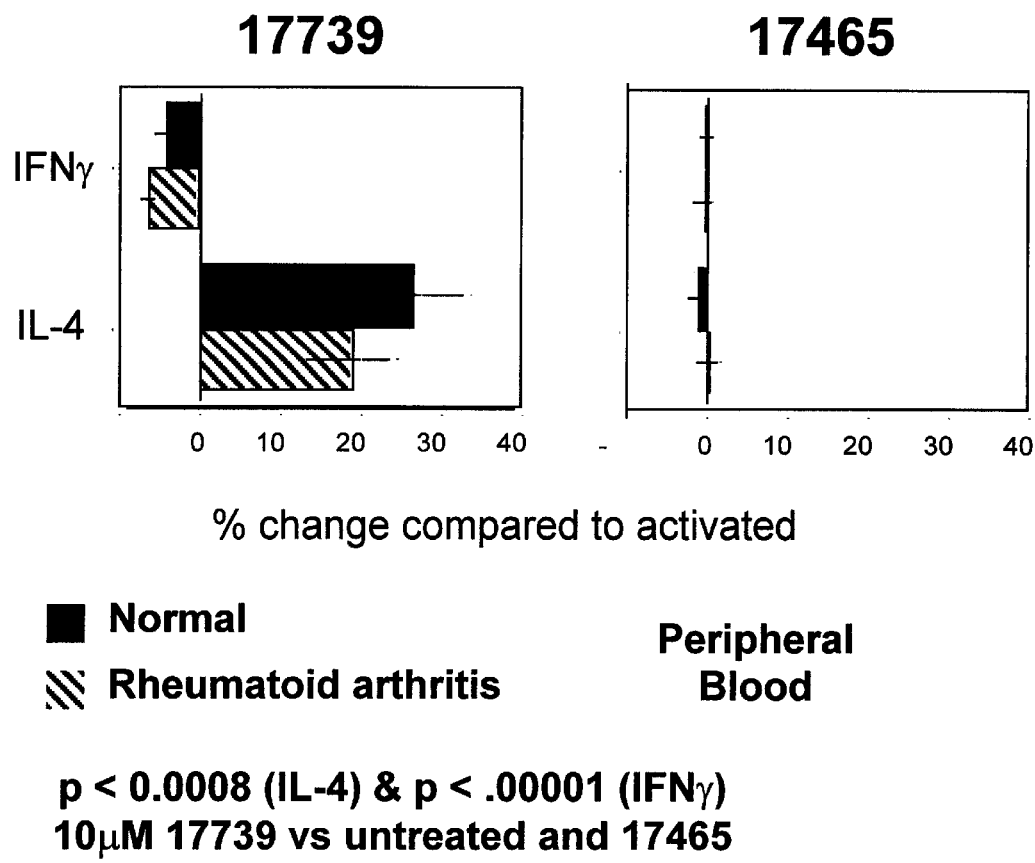
FIG. 28 is a graph depicting induction of Type 2 cytokine bias in T-cells from RA patients and normal donors.
Figure 29:
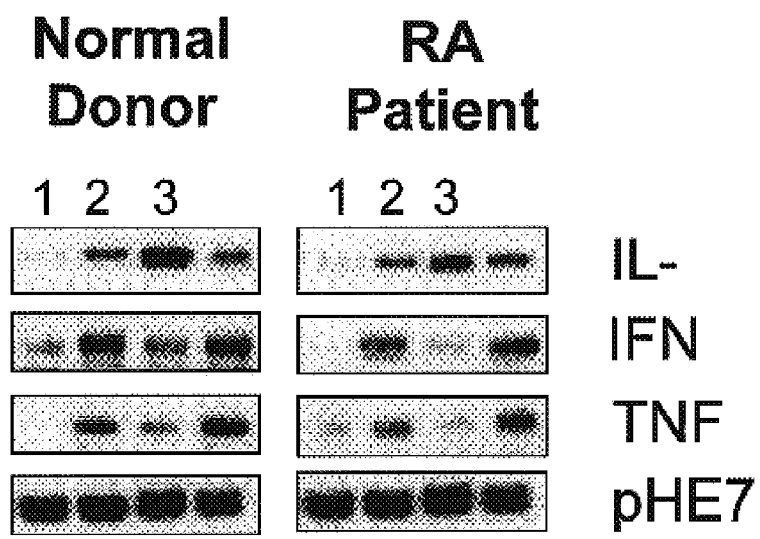
FIG. 29 is an autoradiograph depicting induction of Type 2 cytokine bias in T-cells from RA patients and normal donors.

Consequently it was contemplated, that an induction of a Type 2 bias in patients with diseases characterized at least in part by a Type 1 bias may result in a favorable outcome when such patients were administered ICN 17739. To verify validity of such an approach, T-cells from normal donors and patients suffering from rheumatoid arthritis (RA) were presented with ICN 17739. The results of some of the experiments are shown in FIG. 28, in which Type 1 cytokines are represented by IFN-γ, and Type 2 cytokines are represented by IL-4. Control compound ICN 17465 exhibited under the conditions applied only moderate immunomodulation. The expression patterns of Type 1 and Type 2 cytokines from donors and patients (FIG. 29) confirmed the results from FIG. 28.

Figure 30:
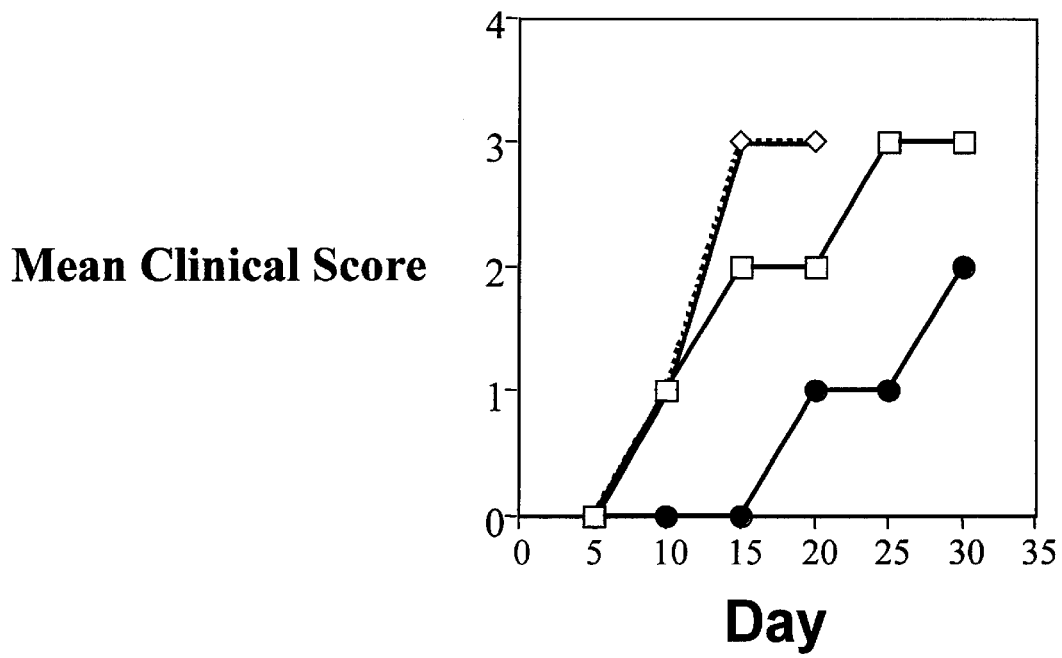
FIG. 30 is a graph depicting prophylactic effect of treatment with contemplated compounds in delayed onset of EAE in mice.
Figure 31:
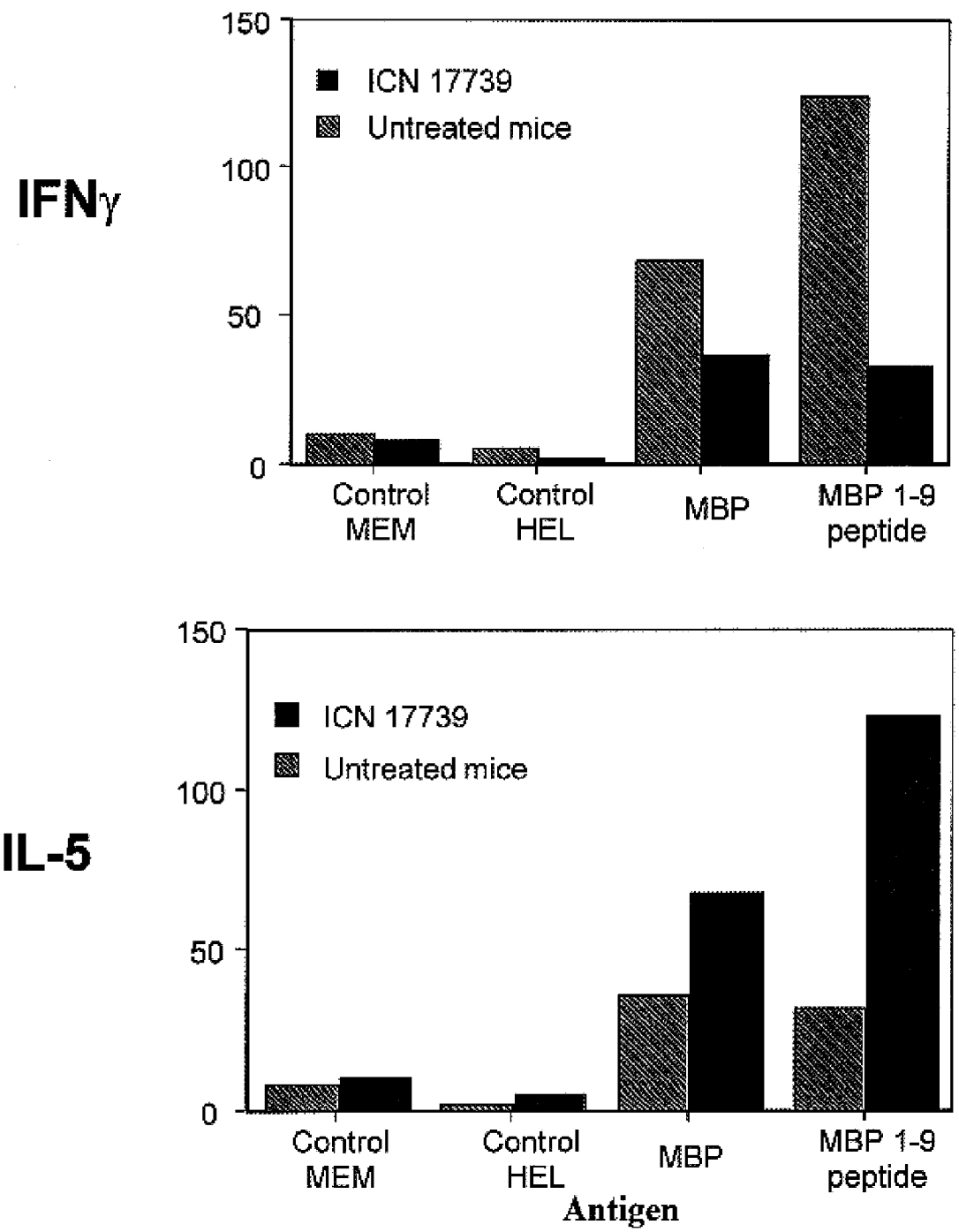
FIG. 31 is a graph depicting induction of MBP-specific Th2 cytokine producing T-cells in mice.

To confirm the induction of a Type 2 bias by contemplated compounds for use in therapy of Type 1 bias diseases, an animal model (murine EAE) of multiple sclerosis (a Type 1 bias-type disease) was employed. B10.PL (H-2u) mice were injected IP daily with ICN 17739 (0.1 mg/kg) for 10d before induction of disease. The mice were immunized SC with 200 μg MBP antigen in complete adjuvant, and injected IV two daily dose of pertussis toxin (200 ng) to induce the disease. Onset and severity of EAE was monitored every other day starting 5 days after MBP injection. The results of these experiments are shown in FIG. 30. ICN 17739 clearly delayed onset of murine EAE, and induces MBP-specific Th2 cytokine producing T-cells as shown in FIG. 31. Consequently, it is contemplated that the compounds according to the inventive subject matter may not only be employed to treat Type 1 cytokine bias (and consequently diseases associated with Type 1 cytokine bias), but also to be of prophylactic use (i.e., to prevent or delay onset and/or severity of diseases associated with Type 1 cytokine bias).

Thus, specific embodiments and applications of pyrrolo [2,3-d]pyrimidine nucleosides and their analogs have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A pharmaceutical composition comprising a compound according to Formula I or a pharmaceutically acceptable salt of the compound according to Formula I

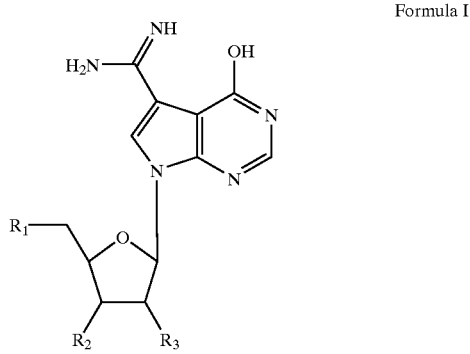

Formula I wherein $R_1$ is OH;

wherein $R_2$ and $R_3$ are OH; and wherein the compound is present in the pharmaceutical composition at a concentration effective to increase expression of a Th2 cytokine of a T-cell relative to a expression of a Th1 cytokine.

2. The pharmaceutical composition according to claim 1 wherein the pharmaceutically acceptable salt is an HCl salt or a HBr salt.

3. The pharmaceutical composition according to claim 1 wherein the Th2 cytokine is interleukin-4 and wherein the Th1 cytokine is interferon gamma.

4. The pharmaceutical composition according to claim 1 wherein the T-cell is from a patient suffering from a disease selected from the group consisting of an autoimmune disease, a cancer, or an infection.

5. A pharmaceutical composition comprising a compound according to Formula I or a pharmaceutically acceptable salt of the compound according to Formula I

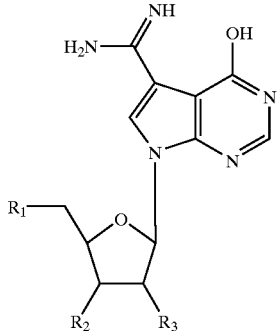

Formula I wherein $R_1$ is OH;

wherein $R_2$ and $R_3$ are OH; and wherein the compound is present in the pharmaceutical composition at a concentration effective to increase expression of an anti-inflammatory cytokine of a T-cell and to decrease expression of an pro-inflammatory cytokine of the T-cell.

6. The pharmaceutical composition according to claim 5 wherein the pharmaceutically acceptable salt is an HCl salt or a HBr salt.

7. The pharmaceutical composition according to claim 5 wherein the anti-inflammatory cytokine is interleukin-10 and wherein the pro-inflammatory cytokine is interleukin-6 or interleukin-1 beta.

* * * * *